US006833707B1

(12) United States Patent
Dahn et al.

(10) Patent No.: US 6,833,707 B1
(45) Date of Patent: Dec. 21, 2004

(54) METHOD AND APPARATUS FOR CHARACTERIZING HIGH-ENERGY ELECTROCHEMICAL CELLS USING POWER FUNCTIONS OBTAINED FROM CALORIMETRY

(75) Inventors: Jeffery R. Dahn, Hubley (CA); Dean D. MacNeil, Halifax (CA); Timothy D. Hatchard, Halifax (CA)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/473,569

(22) Filed: Dec. 29, 1999

(51) Int. Cl.[7] .................... G01N 27/416; H01M 10/48
(52) U.S. Cl. .................... 324/426; 324/427; 429/90
(58) Field of Search ................... 324/426, 427, 324/431, 437, 452, 453; 429/11, 61, 62, 90, 120, 231.95, 231.4; 320/150, 132, 136; 340/636.1; 374/31, 32

(56) References Cited

U.S. PATENT DOCUMENTS

| | | | | |
|---|---|---|---|---|
| 4,622,509 A | * | 11/1986 | Spruijt | 320/130 |
| 5,012,176 A | * | 4/1991 | LaForge | 320/152 |
| 5,587,257 A | * | 12/1996 | Tibbetts et al. | 429/224 |
| 5,642,100 A | | 6/1997 | Farmer | |
| 6,534,954 B1 | * | 3/2003 | Plett | 324/433 |

FOREIGN PATENT DOCUMENTS

| | | |
|---|---|---|
| EP | 0 818 687 | 1/1998 |

OTHER PUBLICATIONS

Vaidyanathan, H. and Rao, G., ("Electrical and thermal characteristics of lithium–ion cells", IEEE, Battery Conference on Applications and Advances, 1999. The Fourteenth Annual, Jan. 12–15, 1999 pp.:79–84).*

Roth E. P. ("Thermal characterization of Li–On cells using calorimetric techniques," Energy Conversion Engineering Conference and Exhibit, 2000 (IECEC) 35th Intersociety, vol. 2, Jul. 24–28, 2000, pp. 962–967 vol. 2).*

MacNeil et al. "An Autocatalytic Mechanism for the Reaction of LixCoO2 in Electrolyte at Elevated Temperature", Journal of Electrochemical Society, 147 (3) pp. 970–979, 1999.*

(List continued on next page.)

*Primary Examiner*—Anjan K. Deb
(74) *Attorney, Agent, or Firm*—Mark A. Hollingsworth; Daniel R. Pastirik

(57) ABSTRACT

Characterizing electrochemical cell components and a response of an electrochemical cell to a specified operating condition involves preparing a sample of an electrode material in contact with an electrolyte. Self-heating, power-temperature or power-time data is obtained for the sample using a calorimetry technique, such as by use of an accelerating rate calorimetry technique or a differential scanning calorimetry technique. A power function is developed for the sample using the self-heating, power-temperature or power-time data. The power function is representative of thermal power per unit mass of the sample as a function of temperature and amount of reactant remaining from a reaction of the sample electrode material and electrolyte. A first power function is developed that characterizes a reaction between the cathode material and the electrolyte in terms of thermal power per unit mass of a cathode sample material, and a second power function is developed that characterizes a reaction between the anode material and the electrolyte in terms of thermal power per unit mass of the anode sample material. An electrode material sample from which a power function is developed is prepared using less than about 100 grams of the electrode material, such as between about 1 and 10 grams, but may be as little as between about 1 milligram and 1 gram. A computer system and computer-readable medium are provided to electronically design and test cells of arbitrary size and shape using power functions developed for individual electrode/electrolyte combinations.

70 Claims, 20 Drawing Sheets

OTHER PUBLICATIONS

Atkins et al. (Physical Chemistry. Fifth Edition).*

International Search Report for PCT/US00/22926, 12/00.

"An Autocatalytic Mechanism for the Reaction of LixCoO2 in Electrolyte at Elevated Temperature" MacNeil, et al. Journal of the Electrochemical Society, vol. 147, No. 3, pp. 970–979. 1999, 8/99.

"Electrochemical–Calorimetric Studies of Lithium–Ion Cells" Hong, et al. Journal of Electrochemical Society, vol. 145, No. 5, May 1998, pp. 1489–1501, 5/98.

"Thermal Properties of Lithium–Ion Battery and Components" Maleki, et al. Journal of the Electrochemical Society, vol. 146, No. 3, pp. 947–954, 10/98.

"Accelerating Rate Calorimetry Study on the Thermal Stability of Lithium Intercalated Graphite in Electrolyte I. Experimental" Richard, et al. Journal of The Electrochemical Society, vol. 146, No. 6, pp. 2068–2077, 10/98.

"Accelerating Rate Calorimetry Study on the Thermal Stability of Lithium Intercalated Graphite in Electrolyte II. Moedling the Results and Predicting Differential Scanning Calorimeter Curves" Richard, et al. Journal of The Electrochemical Society, vol. 146, No. 6, pp. 2078–2084, 10/98.

"Comparison of the Reactivity of Various Carbon Electrode Materials with Electrolyte at Elevated Temperature" MacNeil, et al. Journal of The Electrochemical Society, vol. 146, No. 10, pp. 3596–3602, 4/99.

"The calculation of adiabatic thermal explosion from isothermal DSC measurements" Grewer Thermochimica Acta, vol. 225, pp. 165–176, 1993.

"Thermal modeling and design considerations of lithium–ion batteries" Hallaj, et al. Journal of Power Sources vol. 83, pp. 1–8, 1999.

"Predicting electrical and thermal abuse behaviours of practical lithium–ion cells from accelerating rate calorimeter studies on small samples in electrolyte" Richard, et al.Journal of Power Sources, vol. 79, pp. 135–142, 1999.

"Producing electrical and thermal abuse behaviours of practical lithium–ion cells from accelerating rate calorimeter studies on small samples in electrolyte" Richard, M.M. et al., Journal of Power Sources, 79, 135–142 (1999).

"Accelerating rate calorimetry studies of the effect of binder type on the thermal stability of a lithiated mesocarbon microbead material in electrolyte" Richard, M.N., et al., Journal Power Sources, 83, 1999.

*Accelerating Rate Calorimeter*, Operation, Maintenance and Parts Manual, Columbia Scientific Environmental Instrumentation, Jun. 1996.

*Physical Chemistry*, $5^{th}$ Ed., P.W. Atkins, W.H. Freeman and Company, New York.

*Introduction to Solid State Physics*, $6^{th}$ edition; Kittel, John Wiley & Sons, Inc., New York.

"Carbonic acid, diethyl ester", The National Institute of Standards and Technology (NIST), printed from NIST website on May 22, 2001.

"Ethylene Carbonate", The National Institute of Standards and Technology (NIST), printed from NIST website on May 22, 2001.

* cited by examiner

Figure 7 - Log dT/d versus T for $Li_xCoO$ sample 1 at 4.2 V, initiall heated to a) 150, b) 160, c 170, d) 175 and e) 180°C The dashed lines are th calculations using $E_a$ = 1. eV, $\beta$ = 0.2 and $\gamma$ = 1.9 $10^{16}$ min$^{-1}$.

METHOD AND APPARATUS FOR CHARACTERIZING HIGH-ENERGY ELECTROCHEMICAL CELLS USING POWER FUNCTIONS OBTAINED FROM CALORIMETRY

FIELD OF THE INVENTION

The present invention relates generally to high-energy electrochemical cells, such as lithium-based cells, other secondary cells, and batteries constructed therefrom. More particularly, the present invention relates to systems and methods for characterizing electrochemical cells and for predicting the response of such cells to thermal, mechanical or electrical abuse based on power functions obtained from calorimetry.

BACKGROUND OF THE INVENTION

Rechargeable electrochemical cells are currently used to power a wide variety of portable electronic devices, including laptop computers, cell phones, cameras, and personal organizers, for example. The increased use of such mobile devices has placed a greater demand on the battery manufacturing industry to provide high powered cells that may be used safely in a wide spectrum of consumer and industrial applications. In order to minimize size and weight, battery technologies with high-energy density are normally used. Larger versions of such technologies may, for example, be used in hybrid or all-electric vehicles. High-energy density cells store large amounts of energy in relatively small volumes. If this energy is released quickly and in an uncontrolled manner, however, thermal runaway is possible, leading to safety concerns.

Lithium-ion and lithium-ion polymer cells (collectively referred to as lithium-ion cells in the following discussion), for example, exhibit the largest energy density of all ambient-temperature rechargeable cell technologies. Lithium-ion cells are carefully engineered to meet a variety of safety test standards, including, for example, UL-1642 (Underwriters Laboratories) and IEC-61960 (International Electrotechnical Commission) standards. The tests defined by these standards include oven exposure, short-circuit, forced overcharge, forced discharge, shock and vibration. Other proposed tests include nail penetration tests. It is desirable that cells and batteries constructed from such cells do not emit smoke or flame when subjected to thermal, electrical, and mechanical stress associated with the above-identified tests.

In addition to the electrical energy which lithium-ion cells can deliver during discharge, these and other high-energy cells can also evolve a considerable amount of heat due to the reaction of the electrode materials with the electrolyte. During short-circuiting of a cell, for example, both the electrical energy of the cell and the chemical heat resulting from the electrode/electrolyte reactions are dissipated as heat within the cell. Thermal runaway can occur if the sum of these thermal powers is greater than the power that can be transported from the cell to the environment.

The UL and IEC oven exposure tests probe the severity of electrode/electrolyte reactions. These reactions are most severe when the cell is fully charged. In accordance with these oven exposure tests, a fully charged cell is placed into an oven and exposed to a temperature of 150° C. (UL) or 130° C. (IEC) for a predetermined duration of time. Short-circuiting of the cell under test normally does not occur and the cell temperature rises above the oven temperature to the point where the power generated by electrode/electrolyte reactions is equal to the power that can be transferred to the environment. However, if the former is always larger than the latter, thermal runaway occurs. It is noted that, although cells in consumer use are typically not placed in ovens at high temperature, they may be exposed to 85° C. environments in battery cases that inadvertently are thermally well-insulated. If electrode/electrolyte reactions proceed significantly at such temperatures, insulated batteries could exhibit thermal runaway.

The total power generated by the electrode/electrolyte reactions (under a specific set of circumstances) is proportional to the total volume of the cell. That is, if two cells have the same chemistry, the same construction details and the same charging history, but one has twice the volume of the other, then the larger cell will evolve twice the power due to electrolyte/electrode reactions at elevated temperature than the smaller one. The power that can be transferred to the environment, however, is proportional to the cell surface area. Therefore, it is expected that the cell surface area to volume ratio should be maximized to optimize cell safety. This is not always possible due to cell manufacturing constraints or physical size limitations of a device within which the cell will be housed.

Given the issues discussed above, it can be appreciated that cell designers are faced with a complex task. The cell designer is often asked to maximize cell performance, cell energy density, and cell safety. Design changes that maximize energy density may, however, adversely compromise safety. Design changes to cell shape and cell size also affect safety. Selection of the electrode materials and electrolyte affect performance and safety.

Typically, designers are able to make simple cell performance and energy density estimates based on projections from data collected in lab cells. However, it has heretofore not been possible to reliably predict safety test results of practical cells (e.g., full-scale consumer batteries) based on test results at the lab scale. In order to conduct reliable safety studies, prototyping of a potential product in actual cell hardware, followed by extensive testing, is presently necessary. Moreover, large quantities of electrode materials must be produced in order to properly construct prototype cells for safety testing and evaluation. Conventional cell/battery design and development techniques typically require the production and availability of 10 kilograms or more of sample electrode material. Those skilled in the art readily appreciate that designing, developing, and testing electrochemical cells and batteries, particularly those having a custom, non-industry standard configuration, using conventional approaches is extremely time consuming and costly.

There is a need in the battery manufacturing industry for systems and methods that assist in the design of electrochemical cells and batteries of varying technologies, and which require the production of small quantities of sample electrode materials. There exists a further need for such systems and methods that eliminate the present need to construct full-scale cell/battery prototypes in order to fully evaluate the safety aspects of a given cell/battery design. The present invention fulfills these and other needs.

SUMMARY OF THE INVENTION

The present invention is directed to methods and apparatuses for characterizing electrochemical cell components and for characterizing a response of an electrochemical cell to a specified operating condition. According to one embodiment of the present invention, characterizing electrochemical cell components involves preparing a sample of an electrode material in contact with an electrolyte. Self-heating, power-temperature or power-time data is obtained for the sample using a calorimetry technique, such as by use of an accelerating rate calorimetry technique or a differential scanning calorimetry technique, for example. Obtaining self-heating data, for example, may involve obtaining temperature versus time data of the sample during substantially adiabatic reaction.

A power function is developed for the sample using the self-heating, power-temperature or power-time data. The power function is representative of thermal power per unit mass of the sample as a function of temperature and amount of reactant remaining from a reaction of the sample electrode material and electrolyte.

In general, preparing the electrode material sample involves preparing the sample using less than about 100 grams of the electrode material. According to one embodiment, preparing the electrode material sample involves preparing the sample using between about 1 gram and about 10 grams of the electrode material. In another embodiment, preparing the electrode material sample involves preparing the sample using between about 1 milligram and about 1 gram of the electrode material. Improvements in calorimetry techniques may provide for the development of power functions for electrode material samples using nanograms of the electrode material samples. The electrode material may be a cathode material or an anode material. The electrode material may, for example, include lithium.

In accordance with another embodiment, characterizing electrochemical cell components involves preparing a first sample of a cathode material in contact with an electrolyte and preparing a second sample of an anode material in contact with the electrolyte. First and second self-heating, power-temperature or power-time data are obtained for the first and second samples, respectively, using a calorimetry technique. A first power function for the first sample and a second power function for the second sample are developed using the first and second self-heating, power-temperature or power-time data, respectively. The first power function characterizes a reaction between the cathode material and the electrolyte in terms of thermal power per unit mass of the cathode sample material, and the second power function characterizes a reaction between the anode material and the electrolyte in terms of thermal power per unit mass of the anode sample material.

Preparing the first sample typically involves preparing the first sample using less than about 100 grams of the cathode material, and preparing the second sample typically involves preparing the second sample using less than about 100 grams of the anode material. According to one embodiment, preparing the first sample involves preparing the first sample using between about 1 and 10 grams of the cathode material, and preparing the second sample involves preparing the second sample using between about 1 and 10 grams of the anode material. In another embodiment, preparing the first sample involves preparing the first sample using between about 1 milligram and about 1 gram of the cathode material, and preparing the second sample involves preparing the second sample using between about 1 milligram and about 1 gram of the anode material. The cathode and anode material may each include lithium. The calorimetry technique employed may be an accelerating rate calorimetry technique or a differential scanning calorimetry technique.

According to another embodiment of the present invention, characterizing an electrochemical cell involves defining one or more physical parameters of the electrochemical cell. A first power function characterizing a reaction between a cathode and an electrolyte in terms of thermal power per unit mass of cathode material is provided. Also provided is a second power function characterizing a reaction between an anode and the electrolyte in terms of thermal power per unit mass of anode material. A response of the cell to a specified operating condition is predicted using the first and second power functions and the physical parameters of the electrochemical cell. In one embodiment, characterizing the electrochemical cell in this manner is implemented using a computer and user-interface coupled to the computer.

Defining one or more physical parameters of the cell may further involve adjusting the physical parameters of the cell. Predicting the response of the cell, in this case, involves predicting the response of the cell using the first and second power functions and the adjusted physical parameters of the cell.

Defining one or more physical parameters of the cell may also involve receiving user input data representative of physical parameters of the cell. Receiving user input data may further involve presenting to a user an input field corresponding to each physical parameter of the cell and receiving input data from the user in each of the input fields. Defining one or more physical parameters of the cell may also involve receiving physical parameters of the cell electronically, such as from an external local or remote host processor.

Defining one or more physical parameters of the cell may further involve defining one or more physical parameters for each of an anode and a cathode of the cell. Defining physical parameters for each of the anode and cathode of the cell may further involve adjusting the physical parameters of one or both of the anode and cathode. Predicting the response of the cell in this case further involves predicting the response of the cell using the first and second power functions and the adjusted physical parameters of one or both of the anode and cathode.

The specified operating condition may, for example, include a condition of constant or varying ambient temperature, a condition of a constant or varying current applied to the cell, a condition of an external short-circuit connected to the cell or a condition of a short-circuit internal to the cell.

A system for characterizing an electrochemical cell, in accordance with yet another embodiment of the present invention, includes a processor and a user-interface coupled to the processor. The user-interface includes an input device operable by a user for entering one or more physical parameters of the electrochemical cell. The system further includes memory coupled to the processor. The memory stores a cathode power function characterizing a reaction between a cathode and an electrolyte in terms of thermal power per unit mass of cathode material, and further stores an anode power function characterizing a reaction between an anode and the electrolyte in terms of thermal power per unit mass of anode material. The processor computes a response of an electrochemical cell to a specified operating condition using the cathode and anode power functions and the physical parameters of the electrochemical cell.

The input device is further operable by the user to enter physical parameters of an anode and a cathode of the cell. The processor, according to this embodiment, computes the response of the electrochemical cell to a specified operating condition using the cathode and anode power functions and the user-entered physical parameters of the anode and cathode of the electrochemical cell. The input device is also operable by the user to adjust physical parameters of the cell, and the processor further computes the response of the electrochemical cell to a specified operating condition using the cathode and anode power functions and the adjusted physical parameters of the electrochemical cell. A user may also use the input device to adjust physical parameters of an anode and a cathode of the cell, and the processor computes the response of the electrochemical cell to the specified operating condition using the cathode and anode power functions and the adjusted physical parameters of the anode and cathode of the electrochemical cell.

The system may further include a display. The input device is operable by the user for entering physical parameters of the electrochemical cell into input fields presented on the display. Physical parameters of an anode and a cathode of the electrochemical cell may also be entered using the input device into input fields presented on the display. The system may further include a calorimeter system coupled to the processor. The calorimeter system may include an accelerating rate calorimeter or a differential scanning calorimeter.

The memory of the system may be situated proximate the processor, situated remotely from the processor or distributed at locations local to and/or remote from the processor. The memory that stores the anode and cathode power functions, for example, may be partially or completely situated remotely from the processor. Power functions developed for a number of electrode/electrolyte combinations may be stored in a database or in libraries. Power functions and libraries of power functions may be accessed via a network connection.

Characterizing electrochemical cell components in accordance with another embodiment of the present invention involves defining one or more physical parameters of an electrochemical cell, and characterizing a reaction between a cathode and an electrolyte in terms of thermal power per unit mass of cathode material by defining a first power function. A reaction between an anode and the electrolyte in terms of thermal power per unit mass of anode material is also characterized by defining a second power function. The response of the cell to a specified operating condition is estimated using the first and second power functions and the physical parameters of the electrochemical cell.

Characterizing the respective cathode/electrolyte and anode/electrolyte reactions according to this embodiment involves modeling the respective reactions assuming an autocatalytic reaction mechanism. The first power function, $P_c$, associated with the cathode/electrolyte reaction may be characterized by the following equations:

$$\frac{du}{dt} = k(1-u)(\beta + u^{0.5})$$

$$\frac{dT}{dt} = \frac{h}{C_{tot}} * \frac{du}{dt}$$

where, u represents a dimensionless fractional degree of conversion, k represents a reaction rate constant defined by $k=\gamma \exp(-E_a/k_b T)$, $\gamma$ represents a frequency factor expressed in terms of minutes$^{-1}$, $E_a$ represents activation energy, $k_b$ represents Boltzmann's constant, T represents a temperature of the cell, $\beta$ represents a dimensionless parameter of autocatalysis, h represents total heat which can be evolved by a sample of cathode material during reaction expressed in terms of Joules, $C'_{tot}$ represents a total heat capacity of the reactant and a sample calorimeter bomb expressed in terms of J/K, and H represents total heat generated by the cathode/electrolyte reaction per gram of cathode material.

The second power function, $P_a$, associated with a lithium intercalated carbon anode/electrolyte reaction, may be characterized by:

$$P_B = H_2 \left| \frac{dx_2}{dt} \right| + H_1 \left| \frac{dx_1}{dt} \right|$$

where, $$\frac{dx_2}{dt} = -\gamma_2 \exp^{-E_2/k_b T} x_2^{0.5}$$

$$\frac{dx_2}{dt} = -\gamma_2 \exp^{-E_2/k_b T} x_1 \exp^{-((x_{3o}+x_{2o})+f(x_{1o}-x_1))/(x_{3o}+x_{2o})} \text{ and}$$

$$\frac{dx_3}{dt} = \frac{dx_1}{dt} - \frac{dx_2}{dt}$$

and where, $x_1$ represents an amount of type 1 lithium measured as x in $Li_x C_6$, $x_2$ is an amount of type 2 lithium, measured per six carbons, and $x_3$ is an amount of type 3 lithium, measured per six carbons, $x_{1o}$, $x_{2o}$, and $x_{3o}$ are initial amounts of lithium after electrochemical discharge and before heating, $E_1$ and $E_2$ are activation energies, and $\gamma_1$ and $\gamma_2$ are frequency factors, f is a constant of proportionality that governs how fast the layer of reaction products on the surface of the carbon grows as type 1 lithium is converted to type 3 lithium, and $H_1$ and $H_2$ are the heat per gram of carbon due to the changes $\Delta x_1 = -1$ and $\Delta x_2 = -1$, respectively.

Characterizing the cathode/electrolyte reaction may involve characterizing the cathode/electrolyte reaction using less than about 100 grams of cathode material, and characterizing the anode/electrolyte reaction may involve characterizing the anode/electrolyte reaction using less than about 100 grams of anode material. According to one embodiment, characterizing the cathodelelectrolyte reaction involves characterizing the cathode/electrolyte reaction using between about 1 and 10 grams of cathode material, and characterizing the anode/electrolyte reaction involves characterizing the anode/electrolyte reaction using between about 1 and 10 grams of anode material. In another embodiment, characterizing the cathode/electrolyte reaction involves characterizing the cathode/electrolyte reaction using between about 1 milligram and about 1 gram of cathode material, and characterizing the anode/electrolyte reaction involves characterizing the anode/electrolyte reaction using between about 1 milligram and about 1 gram of anode material. The cathode and anode material may each include lithium.

Characterizing the first and second power functions may involve obtaining temperature versus time data, power versus temperature data or power versus time data for each of the cathode/electrolyte and anode/electrolyte reactions. The first and second power functions are preferably characterized using a calorimetry technique, such as an accelerating rate calorimetry technique or a differential scanning calorimetry technique. The specified operating condition may involve a condition of constant or varying ambient temperature, a condition of a constant or varying current applied to the cell, a condition of an external short-circuit connected to the cell or a condition of a short-circuit internal to the cell.

In accordance with yet another embodiment, a computer readable medium embodying program instructions for characterizing electrochemical cell components is provided. The computer medium embodies program instructions executable by a processor that characterize a reaction between a cathode and an electrolyte in terms of thermal power per unit mass of cathode material by defining a first power function, and further characterize a reaction between an anode and the electrolyte in terms of thermal power per unit mass of anode material by defining a second power function. The program instructions executable by the processor further provide for defining one or more physical parameters of the electrochemical cell, and predicting a response of the cell to a specified operating condition using the first and second power functions and the physical parameters of the electrochemical cell.

According to this embodiment, characterizing the respective cathode/electrolyte and anode/electrolyte reactions involves modeling the respective reactions assuming an autocatalytic reaction mechanism. The first power function, $P_c$, associated with the cathode/electrolyte reaction, and the second power function, $P_a$, associated with the anode/electrolyte reaction, may be respectively computed using the equations provided hereinabove.

Defining one or more physical parameters of the cell may further involve adjusting the physical parameters of the cell, and predicting the response of the cell further involves predicting the response of the cell using the first and second power functions and the adjusted physical parameters of the cell. Defining one or more physical parameters of the cell may also involve receiving user input data representative of physical parameters of the cell. Receiving user input data further may involve presenting to a user an input field corresponding to each physical parameter of the cell, and receiving input data from the user in each of the input fields. Defining one or more physical parameters of the cell may further involve receiving physical parameters of the cell electronically.

One or more physical parameters of the cell may be defined for each of an anode and a cathode of the cell. Defining physical parameters for each of the anode and cathode of the cell may involve adjusting the physical parameters of one or both of the anode and cathode, and predicting the response of the cell involves predicting the response of the cell using the first and second power functions and the adjusted physical parameters of one or both of the anode and cathode. The specified operating condition may involve a condition of constant or varying ambient temperature, a condition of a constant or varying current applied to the cell, a condition of an external short-circuit connected to the cell or a condition of a short-circuit internal to the cell.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
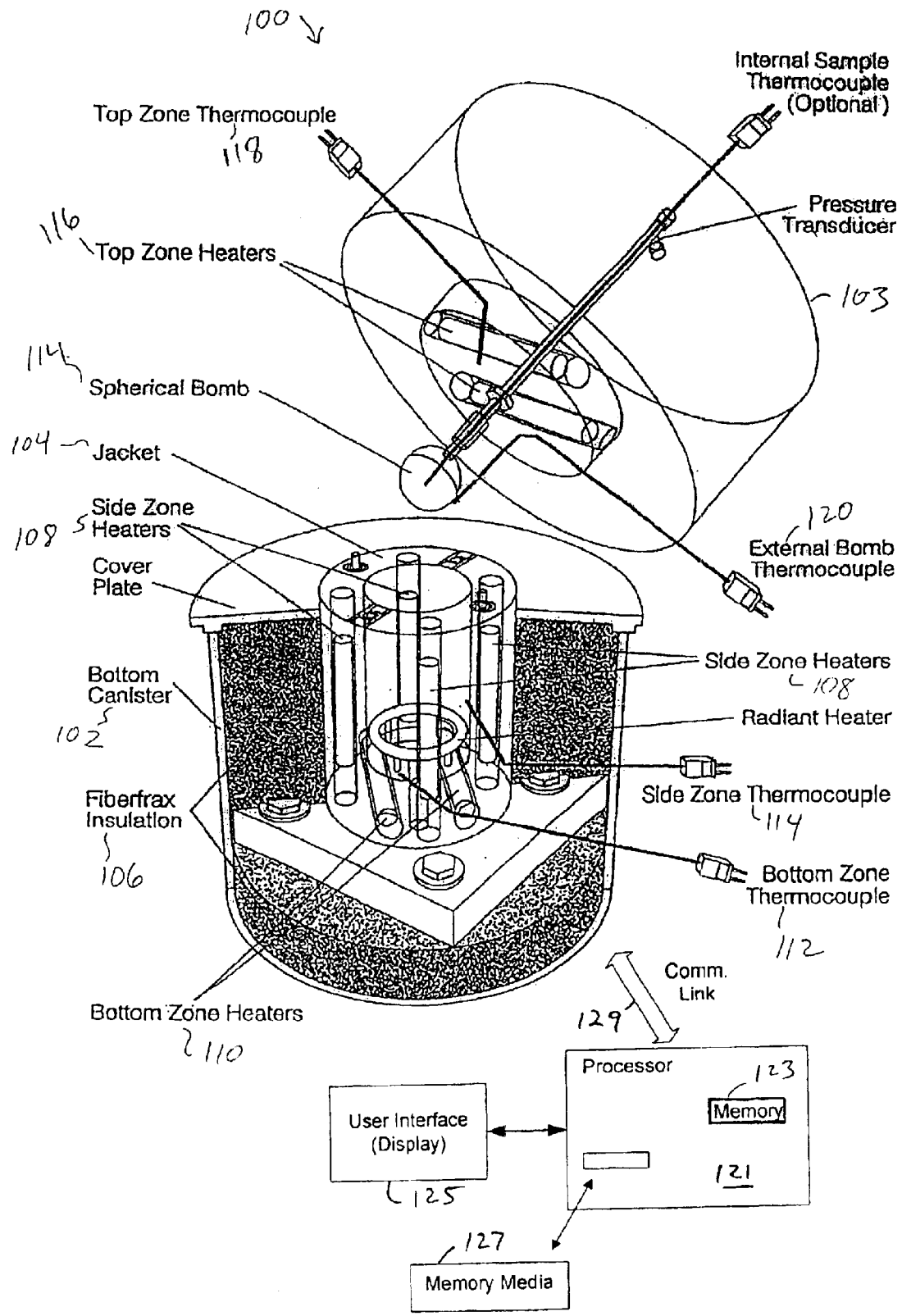
FIG. 1 is a detailed diagram of an accelerating-rate calorimeter which may be used to determine self-heating profiles of electrochemical cell material from which power functions may be derived in accordance with the principles of the present invention.

While the invention is amenable to various modifications and alternative forms, specifics thereof have been shown by way of example in the drawings and will be described in detail hereinbelow. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

In accordance with the principles of the present invention, the response of high-energy electrochemical cells, such as lithium-based cells, to conditions of thermal, electrical and mechanical abuse may be predicted using experimental data collected from calorimetry studies on electrode materials in electrolyte. Accelerating-rate calorimetry or, alternatively, differential scanning calorimetry experiments on small quantities of electrode materials prepared in lab cells may be used to extract mathematical expressions, referred to herein as "power functions," for the particular electrode/electrolyte pair as a function of temperature and chemical reaction history. A power function developed for a particular electrode material may be characterized as the thermal power per gram of electrode material in electrolyte as a function of temperature and amount of remaining reactant, due to the electrode/electrolyte reaction.

The power functions for the positive and negative electrodes of a cell, the thermal conductivity of the cell, the heat capacity of the cell, the mass of electrodes in the cell, and the cell surface heat conductivity may be used to accurately predict the response of a cell of arbitrary size and shape to various safety and performance tests, such as an oven exposure test. Cell response to an overcharge test requires the above described data inputs, as well as electrical power dissipated in the cell. The effect of the R-value of insulation around battery packs may also be readily evaluated. Well-known heat equations and Newton's law of cooling, along with equations and methodologies developed by the inventors as disclosed herein, are used to perform the calculations associated with each of these tests. Methods and apparatuses implemented in accordance with the principles of the present invention will be extremely useful to cell designers and to designers of battery packs, particularly those designed to be incorporated into portable electronics, vehicles, and backup power modules.

Power functions may be developed for a large variety of electrode/electrolyte combinations. These power functions may be organized to form libraries of power functions, which may be organized in many different ways depending on user requirements. The power functions/libraries of power functions may be stored on a permanent storage medium, such as a magnetic or optical storage disk or in an integrated circuit memory or combinational logic device (e.g., non-volatile memory, such as flash memory, electronically erasable programmable read-only memory (EEPROM), gate arrays, and the like). A battery designer may model the performance and response of cells developed from selected electrode/electrolyte combinations by selecting, directly or indirectly, power functions corresponding to the selected electrode/electrolyte combinations from the power function library. One skilled in the art will readily appreciate the substantial time and cost savings that may be realized when designing a cell/battery using a power function-based modeling approach consistent with the principles of the present invention.

By way of further example, a computer system operable by a battery designer may access power functions and/or power function libraries from memory or other processing devices located proximate to or remotely from the designer's computer system. A power function library resource or service may be made accessible to battery designers, from which selected power functions or power function libraries are obtained. Such a service may significantly assist the design and development efforts of numerous battery manufactures. A given battery manufacturer, for example, may access and use established power functions for specified electrode material/electrolyte combinations during the design and evaluation of "virtual" cells of arbitrary size and shape, rather than constructing actual full-scale battery prototypes.

It is noted that, for purposes of simplicity and clarity, aspects of the present invention will be described generally with reference to lithium-ion cells, which is intended to represent any lithium-based cell technology. The methods and apparatuses of the present invention also have utility in overcoming problems associated with thermal runaway of cells having a non-lithium chemistry, such as a nickel-metal hydride, nickel-cadmium, lead-acid, or sodium sulfur-based chemistry, for example. It will be understood that the principles of the present invention are applicable to a wide variety of cell technologies and are not limited to those (e.g., lithium-ion) specifically described herein.

In the development of power functions for a particular cell chemistry, a sample cell is developed using a given electrode material/electrolyte combination. Importantly, this sample cell need only be developed once for a given electrode material/electrolyte combination. From this sample cell, power functions are derived which may be used to characterize various characteristics (e.g., thermal characteristics) of cells of varying shapes and sizes fabricated from the same electrode material/electrolyte combination as that of the sample cell. It is significant that only a relatively small quantity of the sample cell material need be produced for purposes of developing power functions, which may be used to characterize cell components and their response to specified operating conditions (e.g., hostile temperature conditions, a short-circuit condition, an overcharge condition, a nail penetration condition).

As was discussed in the Background, conventional cell/battery design and development techniques typically require the production and availability of 10 kilograms or more of sample electrode material. In stark contrast to such conventional approaches, less than about 100 grams of sample electrode material is required to develop power functions that characterize a given electrode/electrolyte combination in accordance with the present invention. In a preferred embodiment, between about 1 and 10 grams of sample electrode material is required. Preparing sample electrode materials in accordance with the principles of the present invention need be performed only once. After a power function has been determined for a given electrode material/electrolyte combination, this power function is stored for future use. Power functions for a wide variety of electrode material/electrolyte combinations may be developed from such small electrode material samples.

Referring to the drawings, and more particularly to FIG. 1, there is illustrated an embodiment of an accelerating rate calorimeter (ARC) 100 suitable for measuring the self-heating of electrochemical cell samples from which power functions are developed in accordance with the principles of the present invention. The accelerating rate calorimeter 100 shown in FIG. 1 is representative of an apparatus initially developed by the Dow Chemical Company, but later commercialized by Columbia Scientific (model ARC-2000).

The accelerating rate calorimeter 100 maintains a sample in adiabatic conditions once an exothermic reaction has been detected and measures sample temperature as a function of time.

The accelerating rate calorimeter 100 includes a base canister 102 and an upper canister 103 which is detachable with respect to the base canister 102. The base canister 102 includes a nickel-plated copper jacket 104 within which a sample bomb, shown generically in FIG. 1 as spherical bomb 114, is situated when the upper portion 103 is mounted to the base canister 102. The jacket 104 is surrounded by insulation 106 and defines three heating zones, namely, a top, side, and base heating zone, which are provided with heaters 116, 108, and 110, respectively. Each of the heating zones is individually heated and monitored by Nicrosil/Nisil type N thermocouples 118, 114, and 112, respectively, each of which is referenced with respect to an ice point reference.

The canister 102, 103 of the accelerating rate calorimeter 100 is placed within a 1" thick steel shell to provide a barrier in case of an explosion during the experiment. The shell also contains four micro-switches (not shown) that must be depressed before any heat can be provided to the instrument. The sample bomb 114 and bomb thermocouple 120 configuration has been modified from that shown in FIG. 1 due to limitations imposed by the reactive materials of the sample cells described in the Examples provided hereinbelow. The modified bomb 114 is mounted directly onto a thermocouple 120 hanging in the middle of a the jacket 104, in a fishhook-like manner.

The accelerating rate calorimeter 100 measures the self-heating of samples in an adiabatic environment by maintaining the bomb and jacket temperatures exactly equal, thus there is no heat flow to or from the sample. Although these were the ideals set out by the designers, in reality, the calorimeter 100 is at a slightly lower temperature than the sample, so that it does not supply heat to the bomb and an accurate self-heating profile of the sample can be obtained. The change in temperature, $\Delta T$ (K), of the calorimeter 100 during analysis is proportional to the thermal energy released during the exothermic process. The amount of thermal energy, Q (J), released for a particular reaction is proportional to the total specific heat of the reactant(s) and bomb, $C_{tot}$ ($JK^{-1}g^{-1}$), and the mass of reactant(s) and bomb present, $m_{tot}$ (g). These relationships may be combined to give:

$$Q = C_{tot} m_{tot} \Delta T, \quad [1]$$

Equation [1] above governs all reactions taking place in the accelerating rate calorimeter 100. Equation [1] is identical to the total heat capacity, $C'_{tot}$ ($JK^{-1}$), of the sample multiplied by the change in temperature. For a multi-component mixture, such as a sample cell according to the present invention, the total heat capacity of the mixture is equal to the sum of the individual heat capacities, as is given by the following equation:

Total Heat Capacity = $\Sigma$ Individual Heat Capacities [2]

$$C'_{tot} = m_{tot} C_{tot} = \sum_i m_i C_i \quad [3]$$

where, $m_i$ is the mass of component i and $C_i$ is its specific heat. By rearranging Equation [1] above, and solving for temperature and taking the derivative with respect to time, the following self-heating rate of the reaction equation is provided as:

$$dT/dt = dQ/dt [m_{tot} C'_{tot}]^{-1} \quad [4]$$

The quantity dQ/dt is the power, P, (in watts, W) evolved from the sample. The variation in self-heating rates with respect to electrode materials, temperature, and conditions must be understood to properly extract the power functions for a given sample cell according to the present invention.

After proper calibration, the accelerating rate calorimeter 100 is able to determine the self-heating profiles of different samples. The accelerating rate calorimeter 100 is operated in a heat-wait-search (HWS) mode which involves heating to a desired temperature, waiting for thermal equilibrium to be achieved for a set time, then searching for a temperature increase greater than or equal to the set sensitivity (usually 0.02° C./min). If the rate is less than the pre-established sensitivity after the search period, the accelerating rate calorimeter 100 will proceed to the next temperature step and this HWS sequence continues until an exotherm is detected or a stop temperature is reached. If an exotherm is detected, the accelerating rate calorimeter 100 will track it by maintaining adiabatic conditions until the completion of the exotherm. The operator has the ability to change the heating rate, and wait and search times during the setup of the experimental run.

To study the kinetics of the reactions occurring in the accelerating rate calorimeter 100, it is often useful to force accelerating rate calorimeter samples to temperatures above that at which the exotherm is known to onset The initial self heating rates measured as a function of starting temperature may be used to obtain kinetic parameters of importance, which will be discussed in greater detail hereinbelow.

The preparation of one particular sample cell will now be described for purposes of illustration. It is understood that the following description of a sample lithium-ion cell is not to be construed as limiting the scope and applicability of the principles of the present invention as to other electrode/electrolyte combinations. In accordance with the following exemplary embodiment, positive electrode material, $Li_xCoO_2$, and negative electrode material $Li_xC_6$, is prepared, from which a sample coin cell is constructed for each of the electrode materials in combination with a selected electrolyte. Each electrode/electrolyte combination (e.g., $Li_xCoO_2$/ electrolyte and $Li_xC_6$/electrolyte) is then subjected to accelerating rate calorimetry experimentation from which power functions for each electrode/electrolyte combination are derived.

Within the context of this exemplary embodiment, as a lithium-ion cell is charged, lithium atoms leave the $Li_xCoO_2$ positive electrode and intercalate within the carbon of the negative electrode. Both $Li_xCoO_2$ and $Li_xC_6$ react in electrolyte. In order to examine the thermal power produced by each electrode, it is necessary to build accelerating rate calorimeter samples which have only one electrode and electrolyte in contact. This is conveniently accomplished in laboratory coin-type cells, using pellet-shaped electrodes, as described in the following examples.

EXAMPLE #1

Sample electrodes were prepared by combining the electrode powder with 7%, by mass, each of Super S carbon black (MMM carbon, Belgium) and polyvinylidene difluoride (PVDF) binder (9.5% in n-methyl-pyrrolidinone (NMP), National Research Council of Canada (NRC), Ottawa, Canada). The carbon black ensures electrical contact between all of the grains in the electrode, while the binder is used to ensure that the electrode holds together. N-methyl pyrrolidinone is then added in excess to make a slurry. The slurry is poured in a shallow layer and dried at 105° C. to remove the NMP. After drying, the powder was lightly ground in a mortar and then passed through a 300 μm sieve. The subsequent procedure differs for carbon and for $LiCoO_2$, as will be described with reference to FIGS. 2 and 3, respectively.

Figure 2:
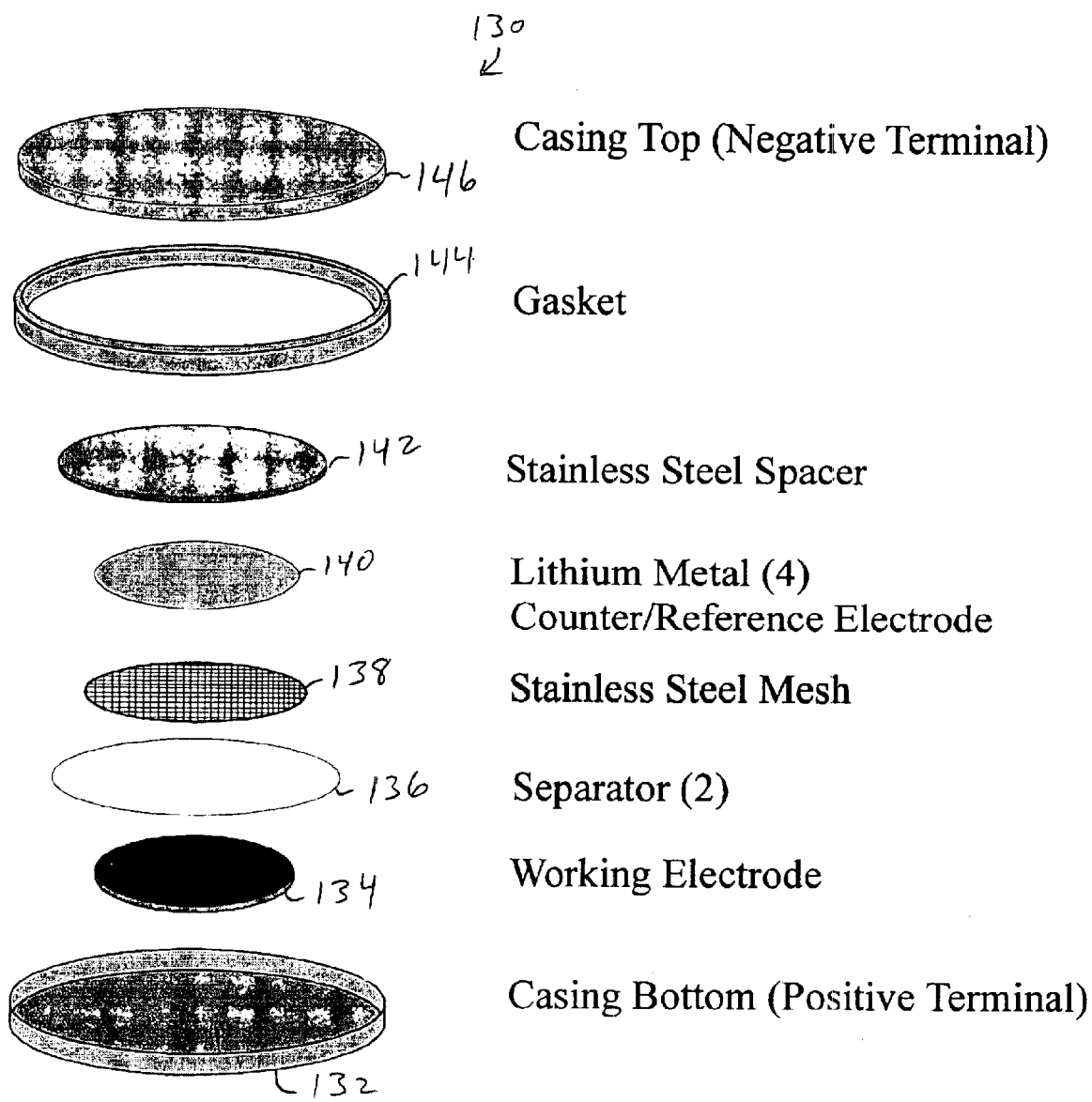
FIG. 2 is a schematic of a coin cell used to prepare carbon electrodes for accelerating rate calorimeter experiments according to an embodiment of the present invention.

Approximately 300 mg of the carbon/binder mixture was then placed in a stainless steel mold to which 2000 psi (13.8 MPa) was applied to produce a 1 mm thick carbon pellet. With reference to FIG. 2, the carbon pellet 134 was then placed in a cell casing bottom 132 and the cell 130 was assembled in a manner depicted generally in FIG. 2 within an argon-filled glovebox. Electrolyte (1M $LiPF_6$EC:DEC 33:67, vol:vol, Mitsubishi Chemicals) was added to the electrode pellet 134 until it was fully wetted, and then two polypropylene separators 136 (Celgard 2502, Celanese) were placed on top of the wet pellet 134. Four pieces of 125 μm thick lithium foil (FMC) 140 were added on top of a stainless steel mesh 138 to ensure fill electrical contact with all of the lithium. A stainless steel spacer 142 was then added above the lithium foil layers 140 to provide pressure on the contents of the cell 130. Finally, the cell top 146, with polypropylene gasket 144, was attached and the cell 130 was crimped shut to seal it from the outside environment.

The lithium/carbon electrochemical cells 130 were fully discharged to 0 V, until the cells' relaxation voltage under open circuit was less than 50 mV after 24 hours. The cells 130 were then transferred to an argon-filled glovebox for accelerating rate calorimeter sample preparation, which will be described in greater detail hereinbelow.

EXAMPLE #2

Figure 3:
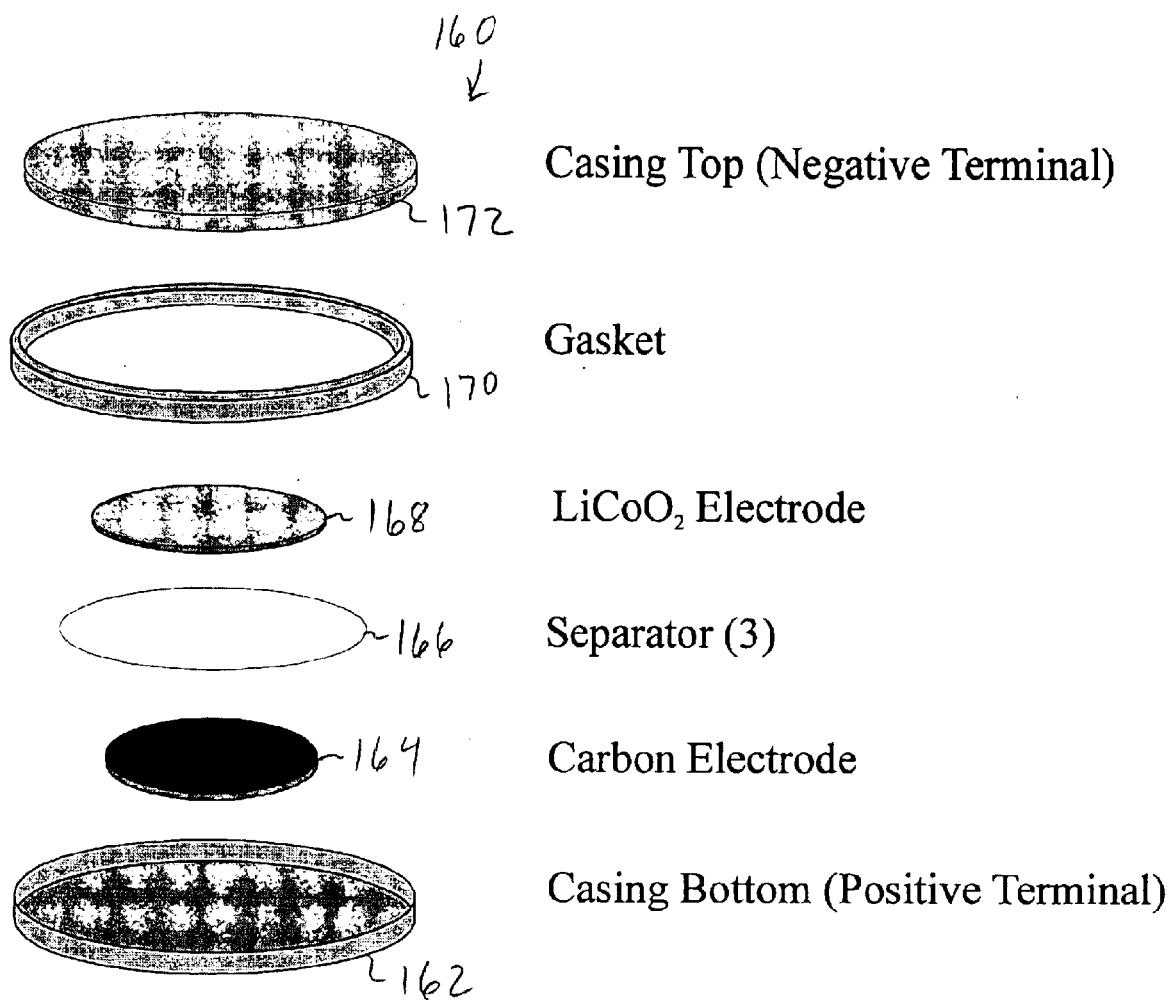
FIG. 3 is a schematic of a lithium-ion coin cell used to prepare $Li_xCoO_2$ for accelerating rate calorimeter samples in accordance with an embodiment of the present invention.

With reference to the cell 160 shown in FIG. 3, 0.75 g of a $LiCoO_2$/binder mixture was placed in a stainless steel mold to which 2000 psi (13.8 MPa) was applied to produce an electrode pellet. Both carbon (made as described above) and lithium cobalt oxide pellets were then transferred to the glovebox, and cells were assembled as depicted generally in FIG. 3. Electrolyte (1M $LiPF_6$EC:DEC 33:67, vol/vol, Mitsubishi Chemicals) was first added to the carbon electrode 164 provided in a casing bottom 162 until fully wetted, and then three polypropylene separators 166 were added on top of it, to which the lithium cobalt oxide pellet 168 was added. A casing top 172 and gasket 170 were added above the lithium cobalt oxide electrode 168, and the can 162, 172 was crimped shut.

When the electrochemical cells 130, 160 were removed from the glovebox, stainless steel tabs were spot-welded to the outer casing and the cells 130, 160 were then connected to a charger system. A variety of experiments were performed with the cells 130, 160 on the charger system to simulate a variety of charging characteristics. After the tests were finished, the cells 130, 160 were transferred to an argon-filled glovebox for accelerating rate calorimeter sample preparation.

Accelerating rate calorimeter samples were enclosed in welded stainless steel type 304 tubes. The tubes had a 0.006" (0.152 mm) wall, a 0.250" (6.35 mm) diameter and a 1.54" (39.1 mm) length. A stainless steel "pocket" made of 0.001" thick foil was attached to the side of the tubes by spot welding. Because of the moisture sensitivity of the samples, a method was developed to seal the tubes in an inert atmosphere. Tungsten Inert Gas (TIG) welding was used to seal the ends of the stainless steel tubes in the glovebox itself.

The electrochemical cells 130, 160 were carefully disassembled in the glovebox and the pellets 134, 164 were recovered. The wet pellets 134, 164 were lightly ground and then each was transferred to the accelerating rate calorimeter sample bomb as described previously with regard to FIG. 1. One end of the bomb had been previously welded shut by Tungsten Inert Gas (TIG) welding. Typically, 350 mg (carbon) or 400 mg ($LiCoO_2$) of the wet electrode was transferred, with an equal amount of excess electrolyte added to the bomb. The bomb was then crimped closed and finally TIG welded shut. The accelerating rate calorimeter sample was mounted in the calorimeter by hooking the pocket of the stainless steel tube over the thermocouple in a fishhook-like manner as discussed previously. The calorimeter was then sealed and experiments were performed.

Figure 4:
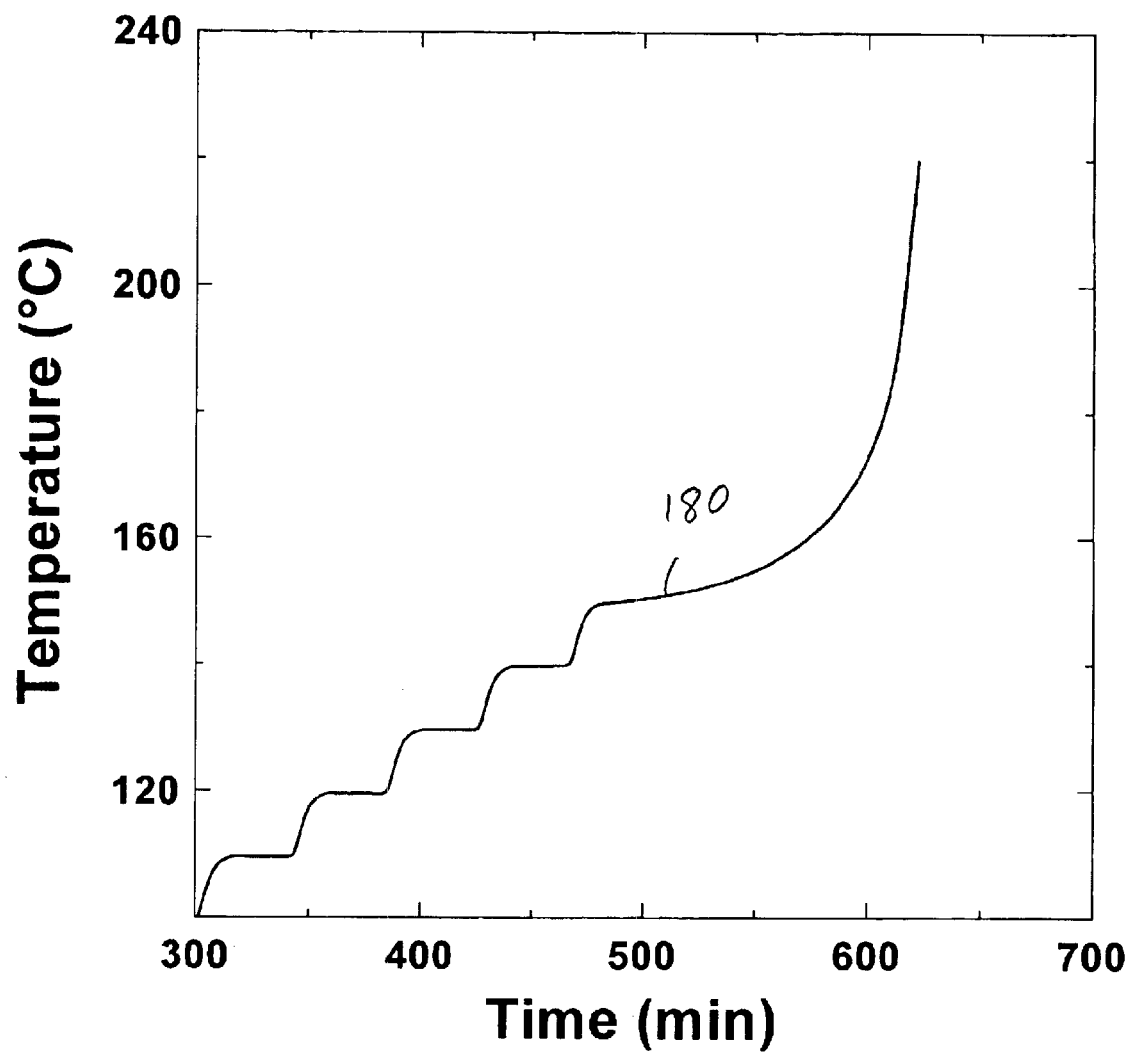
FIG. 4 is a graph of temperature vs. time data for an accelerating rate calorimeter experiment on a $Li_xCoO_2$/electrolyte sample according to an embodiment of the present invention.

FIG. 4 shows typical temperature-time data 180 for an accelerating rate calorimeter experiment on a sample of $LiCoO_2$ charged to 4.2 V versus lithium concentration. At temperatures below 150° C., the accelerating rate calorimeter is in heat-wait-search mode. At 150° C., the self-heating rate is initially above 0.02° C./min, so the accelerating rate calorimeter follows the exotherm under adiabatic conditions. As the sample self-heats, the self-heating rate continually increases as the reaction rate accelerates with increasing temperature.

Figure 5:
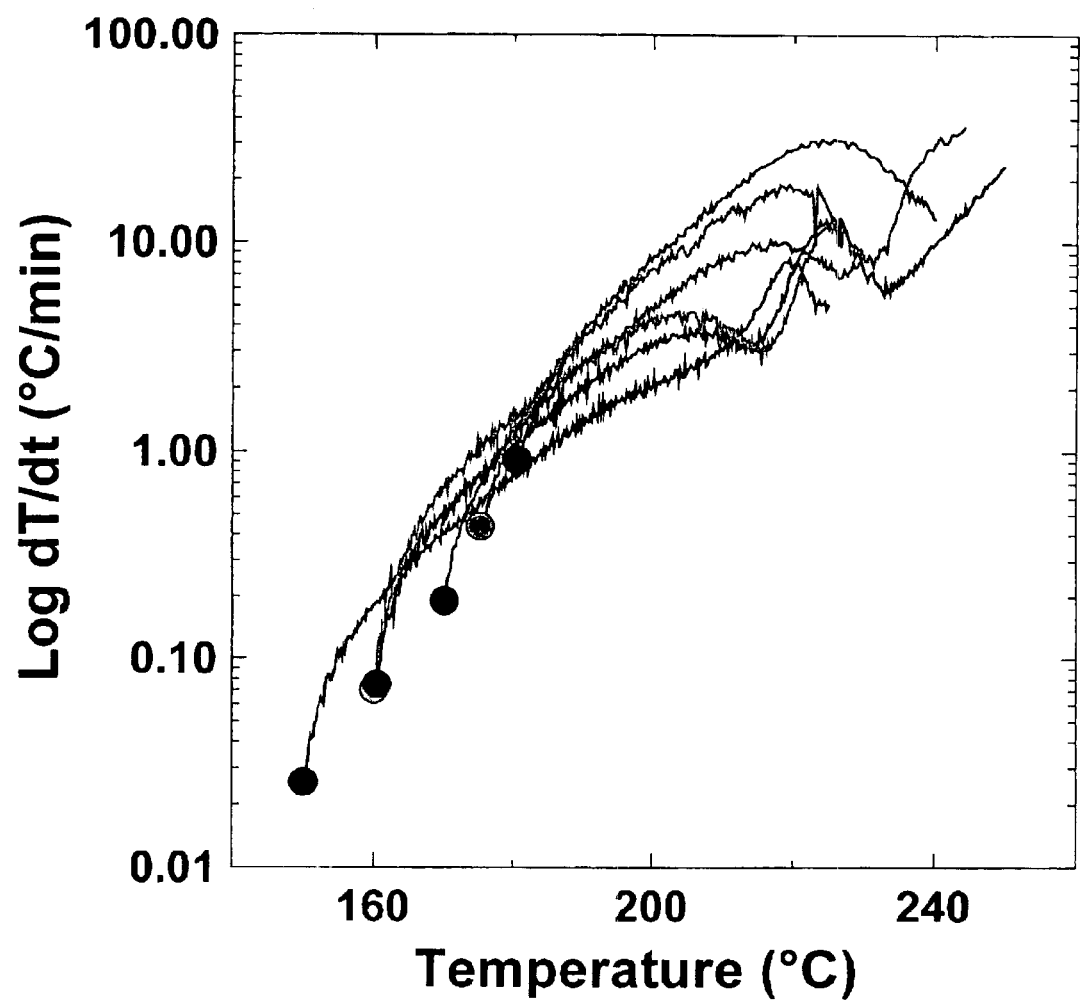
FIG. 5 is a plot of the natural logarithm of the self-heating rate vs. temperature for accelerating rate calorimeter experiments on $Li_xCoO_2$ (4.2 V) in electrolyte heated to various initial starting temperatures in accordance with an embodiment of the present invention.
Figure 6:
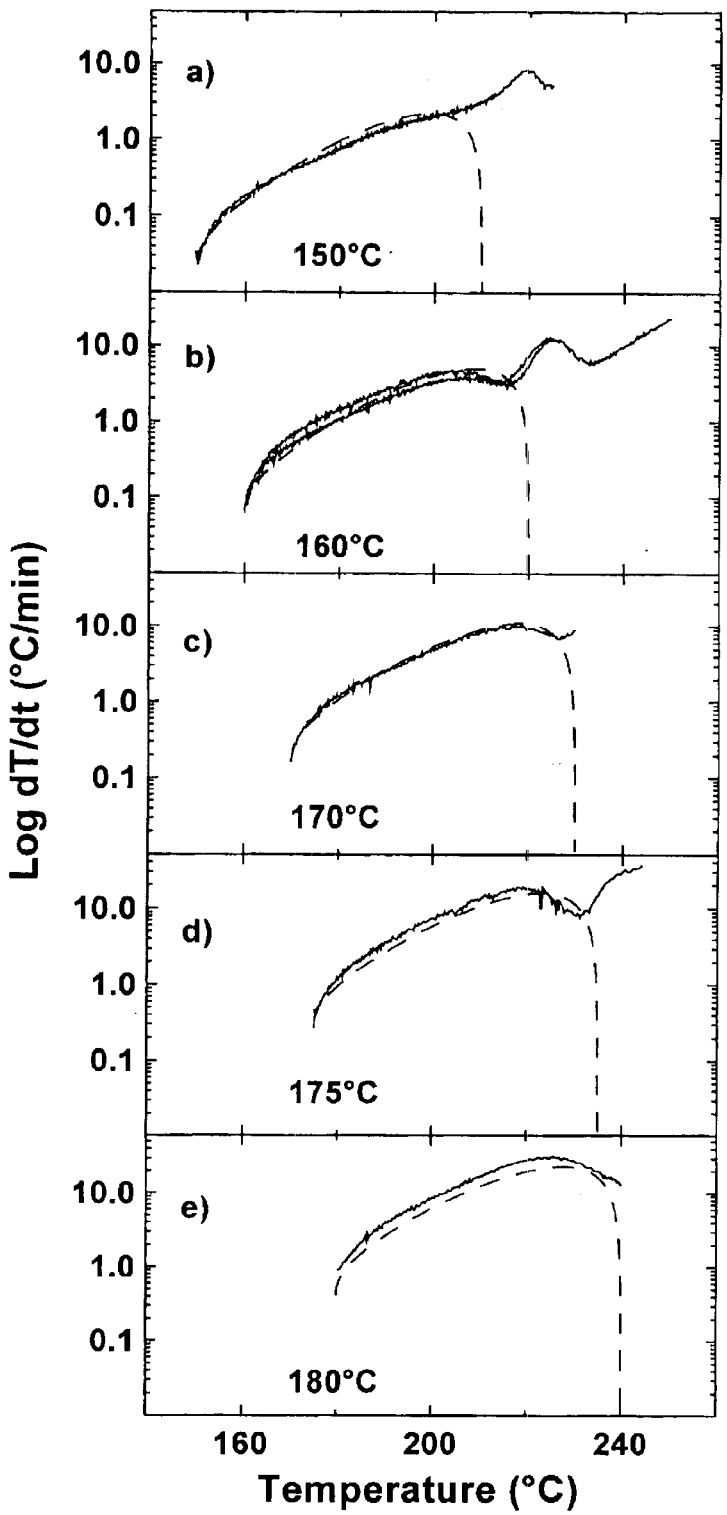
FIGS. 6A–6E are plots of the natural logarithm of the self-heating rate vs. temperature for accelerating rate calorimeter experiments on a $Li_xCoO_2$ sample initially heated to (A) 150° C., (B) 160° C., (C) 170° C., (D) 175° C., and (E) 180° C., respectively, according to an embodiment of the present invention.

To carefully examine the kinetics of the reactions, it is more useful to plot the natural logarithm of the self-heating rate, ln dT/dt, versus T. FIG. 5 shows ln dT/dt versus temperature results for $Li_xCoO_2$ in electrolyte initially heated to a number of starting temperatures. Once accelerating rate calorimeter results of this type have been collected, the power functions can then be obtained, as will now be discussed in further detail.

In general, power functions are derived for individual electrode/electrolyte material combinations. In particular, power functions are obtained for each of the cathode and anode material/electrolyte combinations of a subject cell using accelerating rate calorimetry or differential scanning calorimetry techniques. Once the power functions for particular electrode/electrolyte material combinations are obtained, they are stored for subsequent use. In stark contrast to conventional cell design techniques which require development of full-scale cell/battery prototypes in order to evaluate a given design, power functions obtained from relatively small quantities of sample cell electrode material in accordance with the present invention provide for the characterization and prediction of a cell/battery constructed from like electrode materials having any desired size, shape, weight, form factor, and operating temperature profile.

EXAMPLE #3

In accordance with the following example, power functions for a cathode of a particular chemistry will be described for purposes of illustration. The inventors have performed a careful accelerating rate calorimeter study of the reaction between $Li_xCoO_2$ and electrolyte. Two different samples, referred to hereinbelow as Sample #1 and Sample #2, were studied and found to display similar behavior. In both cases, the reaction of $Li_xCoO_2$ in electrolyte was accurately modeled assuming an autocatalytic reaction mechanism.

In order to model the reaction of the $Li_xCoO_2$ electrode material in electrolyte at 4.2 V, a reaction pathway was hypothesized. The experimental data shown in FIG. 5 suggest a possible autocatalytic mechanism, because the self-heating rate of the 150° C. start temperature sample at 160° C. was larger than an identical sample heated directly to 160° C. Similarly, the self-heating rate of the 160° C. start temperature sample at 170° C. was larger than an identical sample heated directly to 170° C. This behavior is consistent with the acceleration of a reaction by the presence of products as described in the literature (see, e.g., T. Grewer, *Thermochimica Acta,* 225, 165 (1993)). The differential equation describing the autocatalytic model used in the instant example is given by:

$$\frac{du}{dt} = k(1-u)(\beta + u^{0.5}), \quad [5]$$

where, u is the dimensionless fractional degree of conversion, k a reaction rate constant ($k=\gamma \exp(-E_a/k_bT)$), $\beta$ is the parameter of autocatalysis, and $k_b$ represents Boltzmann's constant. The reaction describing this autocatalytic process is given as:

$$B \xrightarrow{A} A + P \quad [6]$$

where, the substance B is converted, in the presence of A, to the product P and A.

Thus, as the reaction continues, the reaction rate increases due to the presence of more A product and then decreases when the amount of B reactant runs out. If u=0 in Equation [5] above, the autocatalytic reaction has not been initiated, and as u increases, the fractional amount of reactant present decreases. A high degree of autocatalysis implies a small value of $\beta$. The temperature influences the kinetics characterized by Equation [2] through the temperature dependence of k The power 0.5 in Equation [5] above implies that the catalyst is most effective at the start of the reaction.

The temperature rise during the autocatalytic reaction is proportional to Equation [5] above and may be characterized by:

$$\frac{dT}{dt} = \frac{h}{C'_{tot}} * \frac{du}{dt}, \quad [7]$$

where, h is the total heat which can be evolved by the sample due to the reaction (Joules) and $C'_{tot}$ is the total heat capacity of the reactant and the bomb ($JK^{-1}$). The term $h/C'_{tot}$ was chosen to correspond to the temperature rise from the onset of the exotherm to the end of the first exothermic behavior ($\Delta T$, 60° C., see, e.g., FIG. 5), because:

$$\int_0^\infty \frac{dT}{dt} dt = \Delta T, \text{ and} \quad [8]$$

$$\int_0^\infty \frac{h}{C'_{tot}} \frac{du}{dt} dt = \frac{h}{C'_{tot}} \Delta u = \frac{h}{C'_{tot}}, \text{ and} \quad [9]$$

since $\Delta u=1$ for the complete consumption of the reactant, thus, $$\Delta T = \frac{h}{C'_{tot}}. \quad [10]$$

FIGS. 6A–6E show that Equations [5] and [7] above may be used to fit the accelerating rate calorimeter results of FIG. 5 closely for a specific choice of the parameters $E_a$, $\gamma$, $\beta$ and $h/C'_{tot}$. FIGS. 6A–6E are plots of the natural logarithm of the self-heating rate versus temperature for accelerating rate calorimeter experiments on the $Li_xCoO_2$ sample of Example #1 above (hereinafter referred to as Sample #1) initially heated to 150° C. (FIG. 6A), 160° C. (FIG. 6B), 170° C. (FIG. 6C), 175° C. (FIG. 6D), and 180° C. (FIG. 6E), respectively. For the fits in FIGS. 6A–6E, the parameters were $E_a=1.6$ eV, $\gamma=1.9\times10^{16}$ min$^{-1}$, $\beta=0.2$ and $h/C'_{tot}=60°$ C.

The model fits only the lowest temperature exothermic process. This process is the one that controls thermal runaway in lithium-ion cells, as will be evident from the discussion provided below. The same model may be used to fit the results of accelerating rate calorimeter experiments on $Li_xCoO_2$ at different voltages in electrolyte. Table 1 below shows the parameters that fit accelerating rate calorimeter results for two different $Li_xCoO_2$ samples at a variety of voltages. The data shown in Table 1 are parameters for the power functions which may be characterized using Equation [11] below derived for the $Li_xCoO_2$ samples of Examples #1 and #2 above at selected voltages versus lithium concentration.

TABLE 1

| Voltage (V) | $E_a$ (eV) | $\beta$ | $\gamma$(min$^{-1}$) | $h/C'_{tot}$ (° C.) | H (J/g) |
|---|---|---|---|---|---|
| Sample 1 - 4.1 | 1.6 | 0.15 | $1.9 \times 10^{16}$ | 60 | 270 |
| Sample 1 - 4.2 | 1.6 | 0.20 | $1.9 \times 10^{16}$ | 60 | 270 |
| Sample 1 - 4.3 | 1.6 | 0.25 | $2.8 \times 10^{16}$ | 60 | 270 |
| Sample 2 - 4.1 | 1.5 | 0.15 | $2.2 \times 10^{15}$ | 75 | 410 |

In order to calculate the power evolved by the reaction of $Li_xCoO_2$ with electrolyte in a practical cell, the reaction power per gram of sample is calculated. The power per gram of $LiCoO_2$ is given by:

$$P_c = H du/dt \quad [11]$$

where, H is the total heat generated by the reaction per gram of $LiCoO_2$ and u and t are as described previously. Using the definition of h in Equation [7] above, H=h/m, where m is the mass of $LiCoO_2$ in the accelerating rate calorimeter sample.

In order to obtain h for Sample #1 of Example #1 above, the value of $h/C'_{tot}=60°$ C. is used, as is the heat capacity of Sample #1. $C'_{tot}$ may be calculated from the specific heats, $c_i$, and masses, $m_i$, of the materials in Sample #1. The specific heats of EC and DEC of the electrolyte and stainless steel were obtained from the literature (Y. S. Touloukian and E. H. Buyco, "*The Thermophysical Properties of Matter-The TRPC Data Series, Volume 5, Specific Heat-Nonmetallic Solids*," Plenum (1970)), and that of $LiCoO_2$ was estimated from the law of Dulong and Petit (see, e.g., C. Kittel, "*Introduction to Solid State Physics*," 7$^{th}$ ed., Wiley and Sons, New York (1996)). For a typical accelerating rate calorimeter specimen of $LiCoO_2$, the heat capacity is approximated by:

$$C_{tot} = \sum_i c_i m_i = 1.0\frac{J}{gK}0.3g + 0.46\frac{J}{gK}0.9g + 1.5\frac{J}{gK}0.4g = 1.3\frac{J}{K} \quad [12]$$

where the terms arising from $LiCoO_2$, stainless steel, and electrolyte are indicated above and it is assumed that the 0.35 g of wet electrode added is made up of 0.3 g $Li_xCoO_2$ and 0.05 g of electrolyte. Therefore, h=60° C. 1.3 J/K=80 J, and H=h/0.3 g=270 J/g. Similar calculations for accelerating rate calorimeter specimens of Sample #2 of Table 1 above give H=410 J/g.

The power function for $Li_xCoO_2$ in electrolyte is now specified. Equation [5] above is used to calculate du/dt and Equation [11] above is used to calculate the evolved power per gram of $Li_xCoO_2$. The parameters provided in Table 1 above are also used. It will be appreciated by one skilled in the art that the parameters of the power functions for other cathode samples may be determined in a similar way. Given the starting value of u, the starting temperature and the thermal boundary conditions, the temperature-time profiles of $Li_xCoO_2$/electrolyte mixtures may be calculated.

EXAMPLE #4

In accordance with the following example, power functions for an anode of a particular chemistry will be described for purposes of illustration. Lithium intercalated carbon prepared electrochemically has three types of lithium atoms: 1) those intercalated within the structure; 2) those incorporated in metastable products on the surface of the carbon due to reactions between lithium atoms and electrolyte; and 3) those in stable reaction products on the surface of the carbon. Lithium atoms of types 1 and 2 can react further with electrolyte as the temperature increases, but type 3 cannot. Lithium atoms of type 1 must pass through the film of reaction products (due to type 2 and type 3 lithium) before they can reach the electrolyte and react. Type 2 lithium atoms become type 3 lithium atoms after reaction. Type 1 lithium atoms become type 3 lithium atoms after reaction as well.

The initial surface layer on the carbon comprising type 2 and type 3 lithium atoms is referred to as the "solid electrolyte interphase" (see, e.g., M. N. Richard and J. R. Dahn, J. Electrochem. Soc. 146, 2078–2086 (1999)), and this layer protects the intercalated lithium from spontaneous reaction with electrolyte. If the temperature becomes large (i.e., greater than about 80° C.), this surface layer begins to decompose (type 2 lithium reacting to become type 3 lithium) and then lithium/electrolyte reactions begin.

Both the reaction of type 2 lithium to become type 3 lithium and the reaction of type 1 lithium to type 3 lithium evolve heat. The power function for $LiC_6$ (mesocarbon micro beads from Osaka Gas) in 1M $LiPF_6$/EC/DEC (33:67 v:v) electrolyte is given by:

$$P_a = H_2\left|\frac{dx_2}{dt}\right| + H_1\left|\frac{dx_1}{dt}\right| \quad [13]$$

where, $$\frac{dx_2}{dt} = -\gamma_2 \exp^{-E_2/k_bT} x_2^{0.5}, \quad [14]$$

$$\frac{dx_1}{dt} = -\gamma_1 \exp^{-E_2/k_bT} x_1 \exp^{-((x_{3o}+x_{2o})+f(x_{1o}-x_1))/(x_{3o}+x_{2o})} \quad [15]$$

and $$\frac{dx_3}{dt} = \frac{dx_1}{dt} - \frac{dx_2}{dt} \quad [16]$$

In Equations [13] to [16] above, $x_1$ is the amount of type 1 lithium measured as x in $Li_xC_6$, $x_2$ is the amount of type 2 lithium, again measured per six carbons, and $X_3$ is the amount of type 3 lithium, again measured per six carbons in the host. The terms $x_{1o}$, $x_{2o}$, and $x_{3o}$ are the initial amounts of lithium after electrochemical discharge and before heating. For carbons from MCMB discharged to 0.0V versus lithium concentration, $x_{1o}$ is about 0.8, $x_{2o}$ is about 0.1, and $x_{3o}$ is about 0.05. The terms $E_1$ and $E_2$ are activation energies, and $\gamma_1$ and $\gamma_2$ are frequency factors. For carbons from MCMB discharged to 0.0V versus lithium concentration, $E_1$ and $E_2$ are about 1.4 eV, $\gamma_1$ is about $4\times10^{15}$ min$^{-1}$, and $\gamma_2$ is about $7.5\times10^{16}$ min$^{-1}$.

The parameter f is a constant of proportionality that governs how fast the layer of reaction products on the surface of the carbon grows as type 1 lithium is converted to type 3 lithium. The term f depends on the carbon surface area. For carbons with a surface area near 1 m$^2$/g, f is near 2 to 5. The terms $H_1$ and $H_2$ are the heat per gram of carbon due to the changes $\Delta x_1=-1$ and $\Delta x_2=-1$, respectively. For carbons from MCMB discharged to 0.0V versus lithium concentration, $H_1$ is about 1700 J/g and $H_2$ is about 600 J/g.

Figure 7:
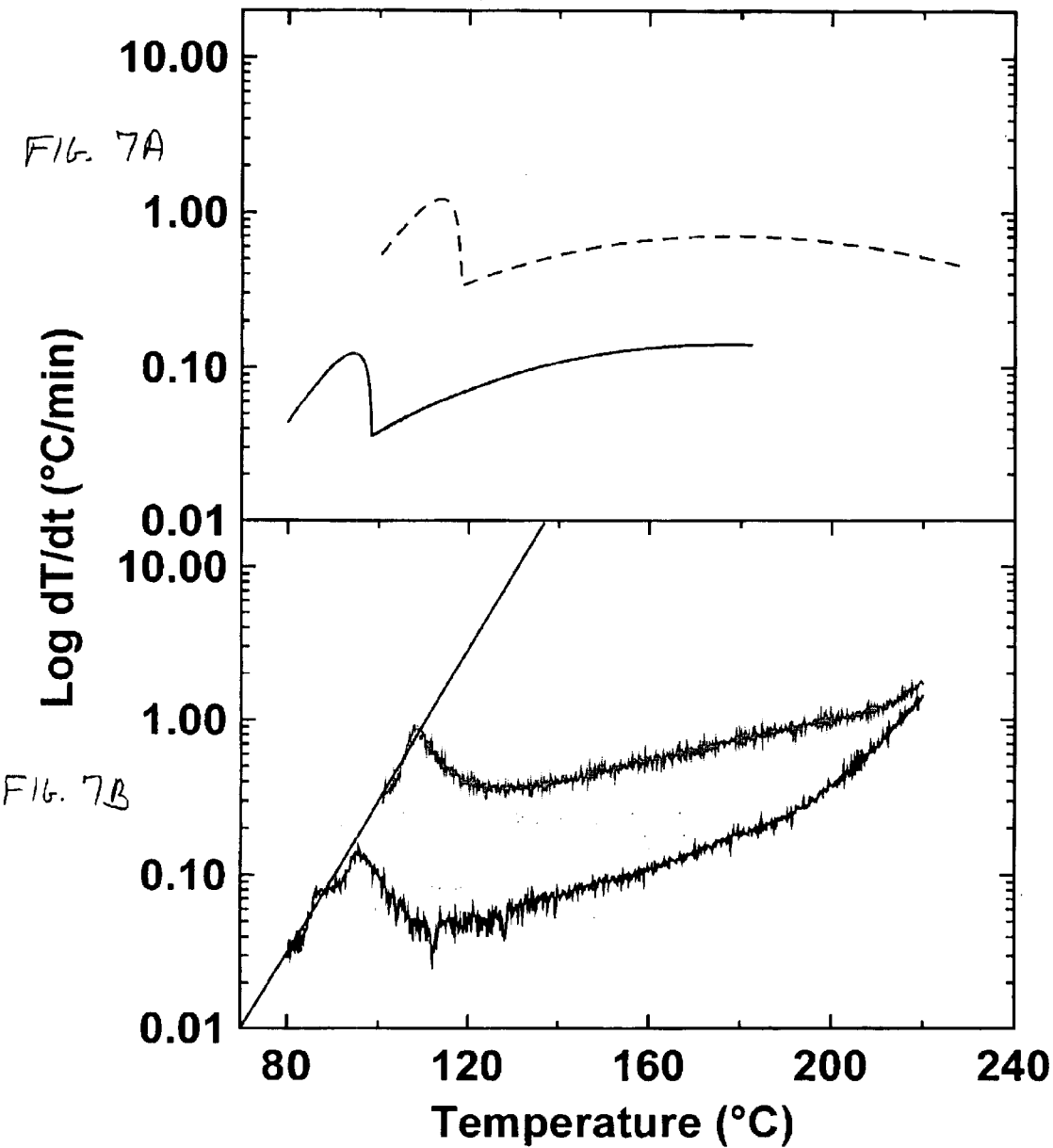
FIGS. 7A–7B show data for lithiated mesocarbon microbeads (MCMB) in electrolyte at two different starting temperatures compared to the calculated profile with particular power function parameters in accordance with an embodiment of the present invention.

Using Equations [4], [12] and [13] above, it is possible to calculate the response of accelerating rate calorimeter samples. FIGS. 7A–7B shows data for lithiated MCMB in electrolyte at two starting temperatures, 80° C. and 100° C., respectively, compared to the calculated profile with the following power function parameters: $x_{1o}$=0.75; $x_{2o}$=0.1; $X_{3o}$=0.033; $E_1=E_2$=1.4 eV; $h_1/C$=400; $h_2/C$=150; $\gamma_1$=4×10$^{15}$; and $\gamma_2$=7.5×10$^{16}$ where, $h_1$ is the heat produced by the accelerating rate calorimeter sample due to the complete reaction of type 1 lithium to type 3 lithium, $h_2$ is the heat produced by the sample due to the complete reaction of type 2 lithium to type 3 lithium, and C is the total heat capacity of the sample plus that of the tube/bomb (referred to previously hereinabove as $C'_{tot}$). It can be seen from FIGS. 7A–7B that agreement between the experimental and prediction data curves is quite good.

As an alternative to using an accelerating rate calorimetry method as described hereinabove, the results of differential scanning calorimetry experiments may be used to extract power functions. According to this approach, a series of differential scanning calorimetry experiments at different scan rates are needed. A differential scanning calorimeter measures the power produced (Watts/g) by a sample as it is heated at a fixed rate. Differential scanning calorimetry experiments typically produce output data in the form of power versus temperature (i.e., power-temperature) data or power versus time (i.e., power-time) data. It has been found, however, that it is difficult to distinguish autocatalytic reactions from simple reactions obeying first order reaction kinetics. Accordingly, the use of an accelerating rate calorimeter approach is preferred, but not required.

Once the electrode/electrolyte power functions are known for a particular electrode/electrolyte combination, the response of full-scale cells of any desired form factor to thermal, mechanical or electrical abuse may be calculated. This is accomplished using a numerical method, assuming radial heat flow, that is, no heat flow through the ends of the can is assumed. It is understood that models other than a radial heat flow model may be assumed, such as a fully-three dimensional heat flow model.

Figure 8:
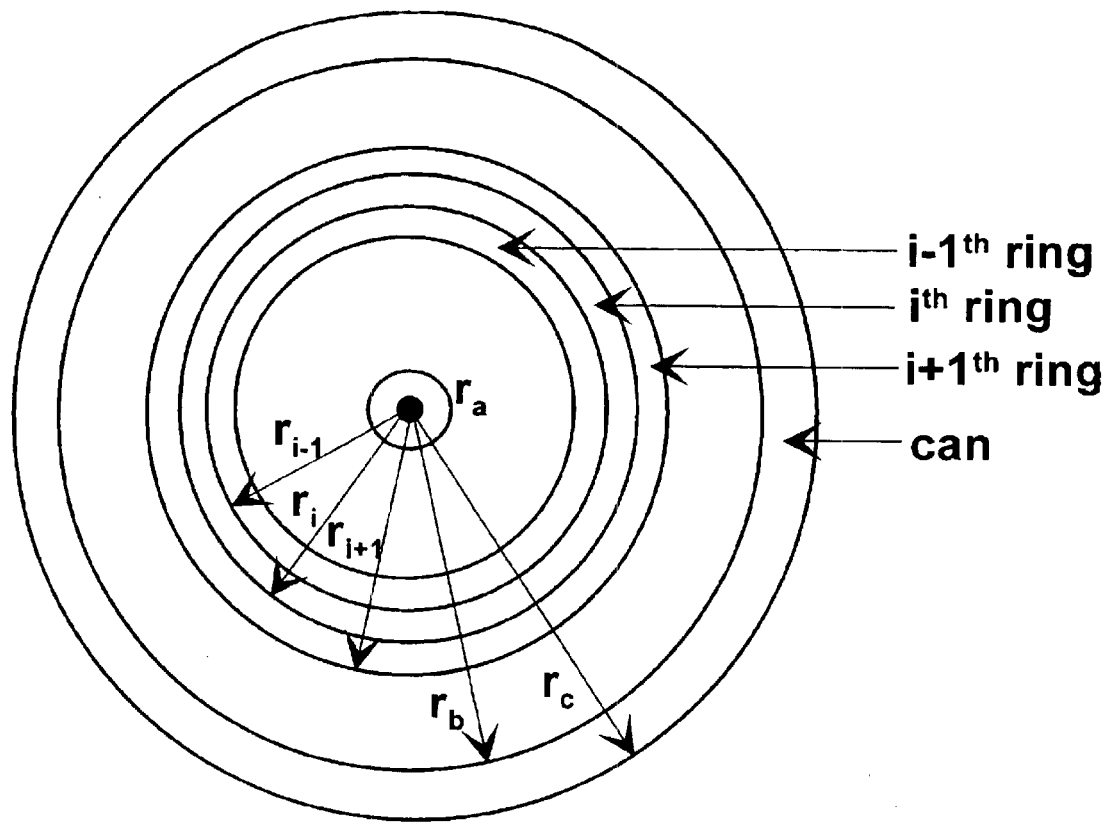
FIG. 8 is a diagram of a cross-section of a cylindrical cell in accordance with an embodiment of the present invention.

FIG. 8 shows a cross-section of a cylindrical cell with the inner, $r_a$, and outer, $r_b$, radii of a jelly roll configured cell. The cell can has inner and outer radii, $r_b$ and $r_c$, as indicated. The jelly roll is then divided into n annular rings of the same thickness. The outer radius of the largest annular ring, $r_n$, is equal to $r_b$. The outer radius of the $i^{th}$ ring is $r_i$ as shown.

For the $i^{th}$ interior ring, the change of temperature, $\Delta T_i$, in a time interval $\Delta t$ is given by:

$$\Delta T_i = \left\{[P_{ai}\rho_a + P_{ci}\rho_c + P_{ei}][\pi L(r_i^2 - r_{i-1}^2)] + \frac{\kappa(T_{i+1} - T_i)2\pi r_i L}{(r_{i+1} - r_i)} + \frac{\kappa(T_i - T_{i-1})2\pi r_{i-1} L}{(r_i - r_{i-1})}\right\}\left\{\frac{\Delta t}{C\rho\pi(r_i^2 - r_{i-1}^2)L}\right\} \quad [17]$$

In Equation [17] above, $P_{ai}$ and $P_{ci}$ are the anode and cathode power functions (per gram of anode material or cathode material, respectively), L is the length of the cylinder, and $\rho_a$ and $\rho_c$ are the average densities of active anode or cathode material per unit volume of jelly roll. The term $P_{ei}$ is the electrical power generated per unit volume of the cell and $\pi L(r_i - r_{i-1}^2)$ is the volume of the $i^{th}$ annular ring. The term $\kappa$ is the average thermal conductivity of the jelly roll material, $T_i$ is the temperature of the $i^{th}$ annular ring, C is the average jelly roll specific heat capacity, and $\rho$ is the average jelly roll density.

The terms in Equation [17] above may be easily understood by one skilled in the art. The first term is the heat added (in time $\Delta t$) to the $i^{th}$ ring by the chemical reactions and by the dissipation of electrical energy. The second term is the heat conducted to the $i^{th}$ ring by its outer neighbor and the third term is the heat conducted to the $i^{th}$ ring by its inner neighbor.

For the ring in contact with the can, the change of temperature, $\Delta T_i$, in a time interval $\Delta t$, is given by:

$$\Delta T_n = \left\{[P_{ai}\rho_a + P_{ci}\rho_c + P_{ei}][\pi L(r_n^2 - r_{n-1}^2)] + \frac{\kappa_{can}(T_{can} - T_n)2\pi r_n L}{(r_c - r_n)} + \frac{\kappa(T_n - T_{n-1})2\pi r_{n-1} L}{(r_i - r_{i-1})}\right\}\left\{\frac{\Delta t}{C\rho\pi(r_n^2 - r_{n-1}^2)L}\right\} \quad [18]$$

where, $\kappa_{can}$ is the thermal conductivity of the can and $T_{can}$ is the can surface temperature.

For the can surface, the change of temperature, $\Delta T_{can}$, in a time interval $\Delta t$ is given by:

$$\Delta T_{can} = \left\{\frac{\kappa_{can}(T_{can} - T_n)2\pi r_n L}{(r_c - r_n)} + (T_e - T_{can})A2\pi r_c L\right\}\left\{\frac{\Delta t}{C_{can}\rho_{can}\pi(r_c^2 - r_n^2)L}\right\} \quad [19]$$

where, A is the can surface heat conductivity per unit area, $2\pi r_c L$ is the surface area of the cell, and $T_e$ is the environmental temperature in which the cell is placed. $C_{can}$ and $\rho_{can}$ are the specific heat capacity and density of the material of the can, respectively. The first term of Equation [19] above is the heat conducted from the can to the outer ring of the jelly roll. The second term is the heat transferred to or from the environment to the cell can.

Equations [17-19] are solved iteratively by computer. Each of the variables describing the anode ($x_1$, $x_2$, and $x_3$) and cathode (u) reaction history are made a function of cell radius, that is $x_1 = x_{1i}$, etc. The initial boundary conditions of the cell are set, that is, $T_e$ and each $T_i$ are initialized, and each of $x_{1i}$, $x_{2i}$, $X_{3i}$ and $u_i$ are set to their initial values.

For purposes of illustration, it is assumed that for a 150° C. oven exposure test with a fully charged (4.2 V) cell at room temperature placed instantly into a heated oven, one would set: $T_e$=150° C., $T_{can}$=21° C., $T_i$=21° C. for all i, $u_i$=0 for all i, $x_{1i}$=0.8 for all i, $x_{2i}$=0.1 for all i, and $x_{3i}$=0.05 for all i. Small time intervals (e.g., 0.1 second) are taken and Equations [5, 11, 13–19] above are used to calculate the changes in the reaction history parameters and the temperatures of the annuli in the small time intervals. These changes are added to the initial values and the calculation is repeated numerous times, until the reactions cease due to the depletion of reactants (i.e., both u=1 and $x_1$=0 for all rings) or until one is satisfied that no runaway reaction will occur. A computer program implementing this model has been reduced to practice using both a Fortran program and a Visual C++ program.

Figure 9:
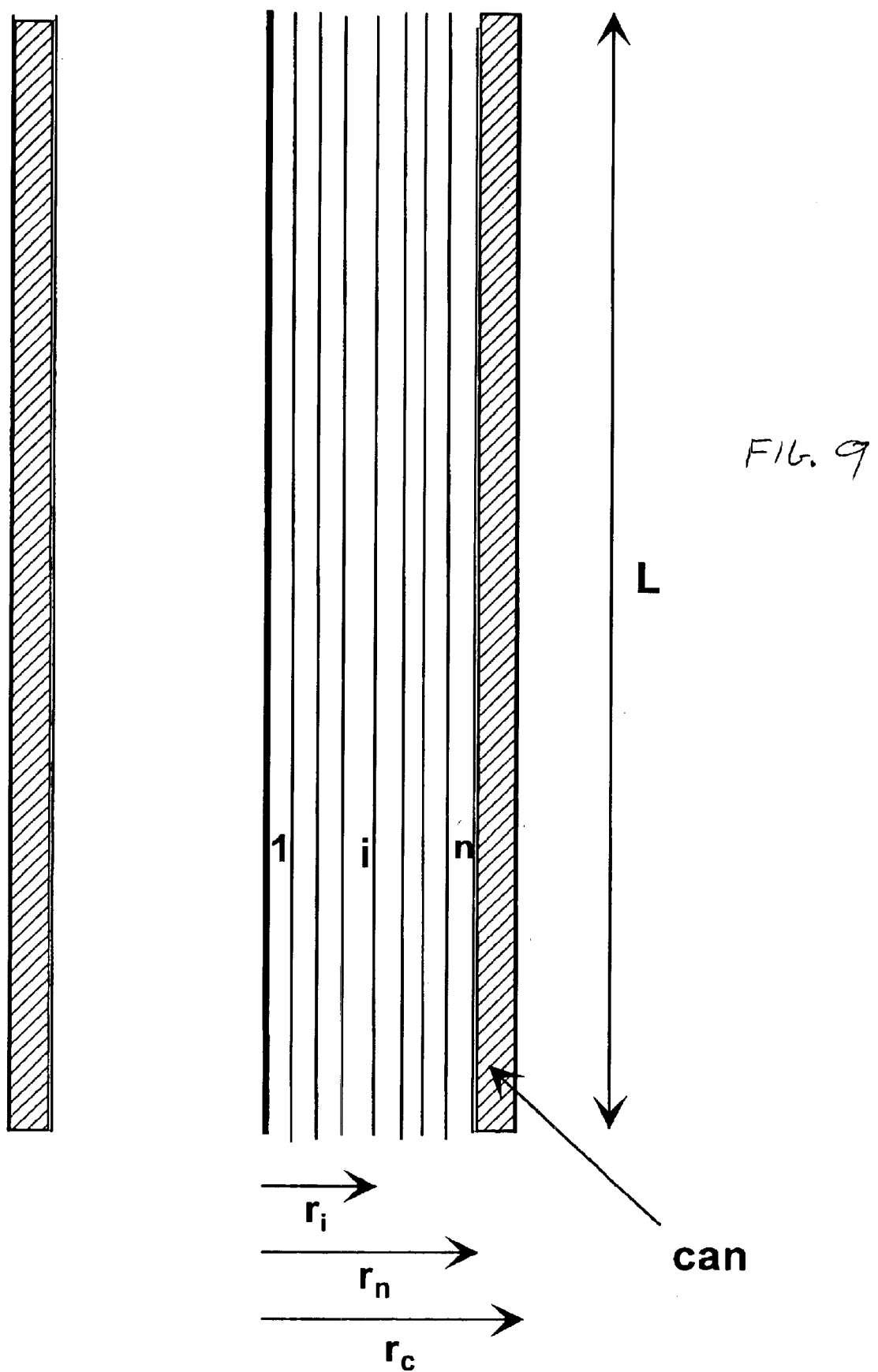
FIG. 9 is a cross-section of a prismatic cell used for thermal modeling in accordance with an embodiment of the present invention.

Equations [17-19] are easily modified for planar geometry, assuming that heat flows only perpendicular to the plane of the cell. This assumption is valid in cases commonly found in prismatic lithium-ion and lithium-ion polymer cells, where the cell thickness is normally less than one tenth the cell length or width. FIG. 9 shows a cross-section of a prismatic cell. The cell has a length, L, a width, W, and a thickness, $2r_c$. The cell stack has a total thickness of $2r_n$. The cell stack is divided into 2n slabs as indicated in the drawing. In cases where there is symmetric heating or cooling at the cell surface, there will be no flow of heat across the center of the cell, which is denoted by the heavy line.

For the $i^{th}$ interior slab, the change in temperature, $\Delta T_i$, which occurs in time $\Delta t$, is (by analogy to the cylindrical cell) given by:

$$\Delta T_i = \left\{[P_{ai}\rho_a + P_{ci}\rho_c + P_{ei}][LW(r_i - r_{i-1})] + \frac{\kappa(T_{i+1} - T_i)WL}{(r_{i+1} - r_i)} + \frac{\kappa(T_i - T_{i-1})WL}{(r_i - r_{i-1})}\right\}\left\{\frac{\Delta t}{C\rho W(r_i - r_{i-1})L}\right\} \quad [20]$$

If, i=1, then the third term on the right-hand side of Equation [20] is omitted to account for the lack of heat flow to the center of the cell.

For the $n^{th}$ interior slab the change in temperature, $\Delta T_n$, which occurs in time $\Delta t$, is (by analogy to the cylindrical cell) given by:

$$\Delta T_i = \left\{[P_{ai}\rho_a + P_{ci}\rho_c + P_{ei}][LW(r_n - r_{n-1})] + \frac{\kappa(T_{can} - T_n)WL}{(r_c - r_n)} + \frac{\kappa(T_n - T_{n-1})WL}{(r_n - r_{n-1})}\right\}\left\{\frac{\Delta t}{C\rho W(r_n - r_{n-1})L}\right\} \quad [21]$$

For the can surface, the change of temperature, $\Delta T_{can}$, in a time interval $\Delta t$ is given by:

$$\Delta T_{can} = \left\{\frac{\kappa_{can}(T_{can}-T_n)WL}{(r_c-r_n)} + (T_e-T_{can})AWL\right\}\left\{\frac{\Delta t}{C_{can}\rho_{can}W(r_c-r_n)L}\right\} \quad [22]$$

Equations [20–22] above are solved iteratively by computer. Each of the variables describing the anode ($x_1$, $x_2$, and $X_3$) and cathode (u) reaction history are made a function of cell thickness, that is, $x_1 = x_{1i}$, etc. The initial boundary conditions of the cell are set, that is, $T_c$ and each $T_i$ are initialized, and each $x_{1i}$, $x_{2i}$, $X_3$; and $u_i$ are set to their initial values. As an example, for a 150° C. oven exposure test, with a fully charged (4.2 V) cell at room temperature placed instantly into a heated oven, one would set: $T_e = 150°$ C., $T_{can} = 21°$ C., $T_i = 21°$ C. for all i, $u_i = 0$ for all i, $x_{1i} = 0.8$ for all i, $x_{2i} = 0.1$ for all i and $x_{3i} = 0.05$ for all i. Small time intervals (e.g., 0.1 second) are taken and the Equations [5, 11, 13–16, 20–22] above are used to calculate the changes in the reaction history parameters and the temperatures of the slabs in the small time intervals. These changes are added to the initial values and the calculation is repeated many times, until the reactions cease due to the depletion of reactants (i.e., both u=1 and $x_1 = 0$ for all rings) or until one is satisfied that no runaway reaction will occur.

In order to confirm the predictive power of the method described above, accurate temperature-time data for cylindrical lithium-ion cells placed into a heated oven must be obtained. According to one approach, a VWR Scientific 1330 GM gravity convection oven is used. The oven has a 3" diameter hole centered in its top, through which cells may be lowered via an attached thermocouple. A second thermocouple is placed in a small brass block on the oven shelf to monitor the oven temperature. The oven is allowed to equilibrate at the test temperature for at least 4 hours, and the oven temperature stabilizes to within ±0.2° C. of the set temperature.

The cell thermocouple is tied to the cell with 3 small wires, like twist ties. A small amount of Wakefield's Thermal Compound is placed at the site where the thermocouple junction touches the cell to ensure good thermal contact therebetween. The thermocouple junction is then covered with a small amount of glass wool.

At the beginning of the test, the cell with attached thermocouple is lowered into the stabilized oven and hung in the center of the oven. The cell is at least 5 cm away from any oven shelf or wall. Then the oven and cell temperatures are measured automatically by computer until thermal runaway occurs or for 24 hours, which ever occurs first.

In order to use Equations [17–22] above, a variety of parameters are needed. These include the surface heat conductivity per unit area, A, the cell thermal conductivity, κ, and the jelly roll specific heat, C. The surface heat conductivity, A, was measured by experiments using solid stainless steel, brass or aluminum cylinders of known radius, r, length, L, mass, m, specific heat, C, and density, ρ. A thermocouple was attached to the cylinder, and the cylinder was lowered into the oven. The temperature of the cylinder was measured as a function of time. Assuming that the temperature within the cylinder is uniform (it is a good approximation since the thermal conductivity of metals is large), the following is obtained for the oven temperature versus time:

$$AL2\pi r(T_e-T) = CmdT/dt \quad [23]$$

where, $T_e$ is the environment temperature (oven temperature) and T is the cell temperature.

Rearranging Equation [23] above gives:

$$dT/dt = 2A(T_e-T)/(rCp) \quad [24].$$

A plot of dT/dt versus $(T_e-T)$ yields $2A/(rCp)$ as the slope. Since C and ρ are known for common metals, A is determined. A=0.00127 W/(cm² K) is measured for stainless steel.

It is understood that surface heat conductivity depends on the details of the surface. For example, a stainless steel cylinder wrapped with a cell label has surface heat conductivity that is different from that of a bare stainless steel cylinder (i.e., cylinder without the label). In such a case, an actual label used on an actual cell may, for example, be applied to a known cylinder and the surface heat conductivity may be determined therefrom.

The thermal conductivity of the jelly roll were taken from literature values (H. Maleki, A. Said, J. R. Selman, R. Dinwiddie, H. Wang, *J. Electrochem. Soc.*, 146 947 (1999)). The heat capacity of 18650 cells from manufacturer A were also obtained from the manufacturer. These parameters may be measured for arbitrary cells using the methods described in H. Maleki, A. Said, J. R. Selman, R. Dinwiddie, H. Wang, *J. Electrochem. Soc.*, 146 947 (1999).

EXAMPLE #5

In the following example, oven exposure test results were calculated and compared to predicted results obtained in accordance with the principles of the present invention. MCMB and $LiCoO_2$ powders were obtained from battery manufacturer A. These powders are believed to be the similar to those used in 18650 size lithium-ion cells produced by that manufacturer. Using the accelerating rate calorimeter, power functions for the anode/electrolyte (0 V) and cathode/electrolyte (4.2 V) reactions were determined as described above. The power functions are given by Equation [7] for the cathode/electrolyte reaction and Equation [13] for the anode electrolyte reaction. The parameters used for these power functions are listed in Table 2 below.

TABLE 2

| Portion of Model | Parameter | Value | Units |
|---|---|---|---|
| Cathode/electrolyte | | | |
| | H | 270 | J/g |
| | γ | 1.9 × 10¹⁶ | min⁻¹ |
| | β | 0.2 | unitless |
| | $E_a$ | 1.6 | eV |
| Anode/electrolyte | | | |
| | $H_1$ | 1700 | J/g |
| | $\gamma_1$ | 4 × 10¹⁵ | min⁻¹ |
| | $E_1 = E_2$ | 1.4 | eV |
| | $x_{10}$ | 0.75 | unitless |
| | F | 4.5 | unitless |
| | $H_2$ | 600 | J/g |
| | $\gamma_2$ | 7.5 × 10¹⁶ | min⁻¹ |
| | $x_{20}$ | 0.1 | unitless |
| | $x_{30}$ | 0.05 | unitless |
| Cell | | | |
| | A | 0.00127 | W/(cm²K) |
| | C (ref. 13) | 0.75 | J/(gK) |
| | $r_c$ | 0.90 | cm |
| | $r_n$ - (N.B. the can was neglected in this calc.) | 0.90 | cm |
| | ρ | 2.68 | g/cm³ |
| | $\rho_a$ | 0.36 | g/cm³ |

TABLE 2-continued

| Portion of Model | Parameter | Value | Units |
|---|---|---|---|
| | κ | 0.034 | W/(K cm) |
| | $\rho_c$ | 0.72 | g/cm$^3$ |

Figures 10A, 10B:
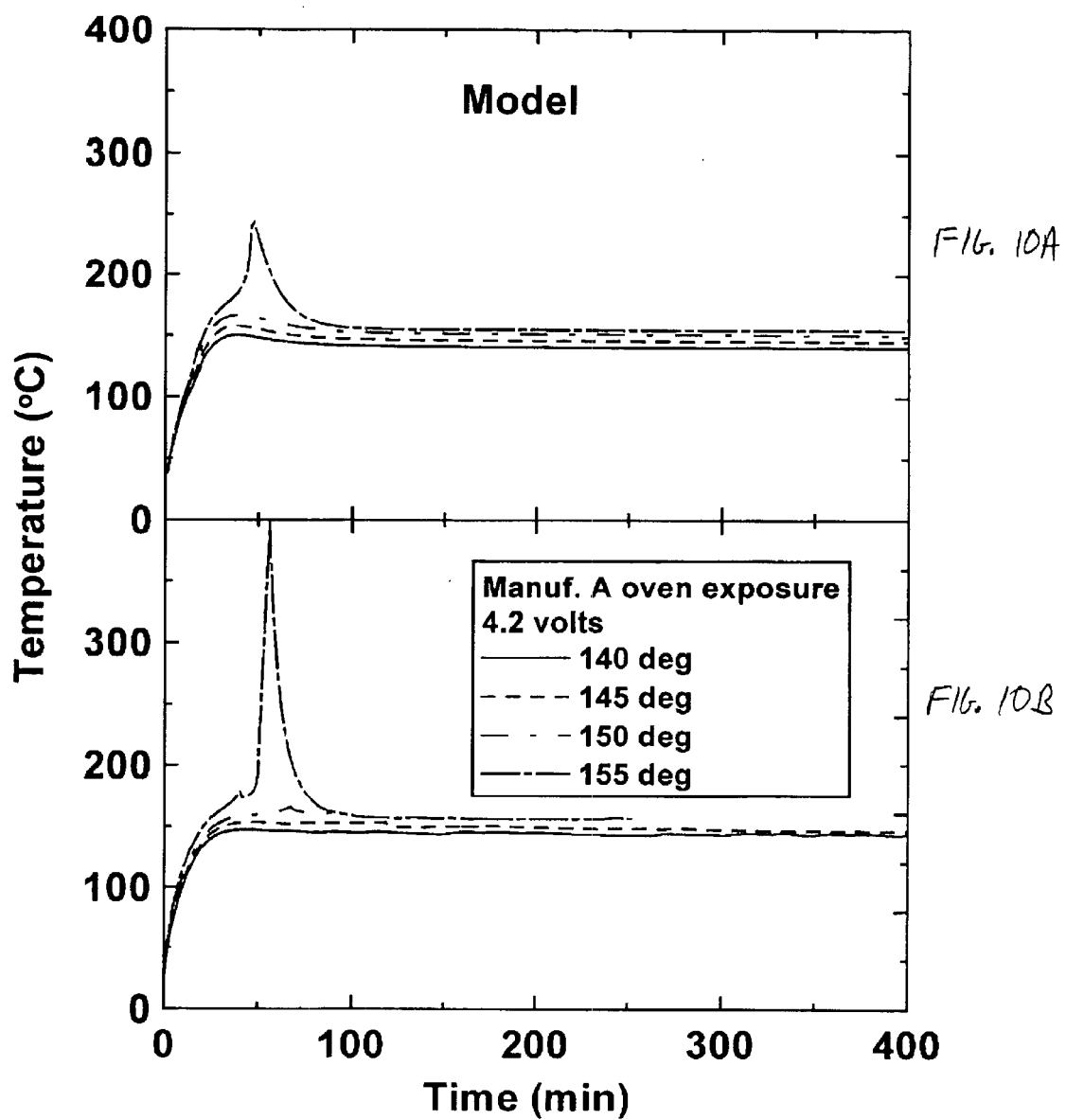
FIGS. 10A–10B are temperature vs. time graphs illustrating a comparison of the calculated and measured oven-exposure profiles for cells from a first manufacturer (Manufacturer A) according to an embodiment of the present invention.

Oven exposure test predictions were made using these power functions and Equations [17–19] with $P_e$=0.0. Oven temperatures of 140° C., 145° C., 150° C. and 155° C. were simulated. FIG. 10A shows the results.

Oven exposure experiments were made on 18650 size lithium-ion cells from manufacturer A. Start temperatures of 140° C., 145° C., 150° C. and 155° C. were used. The experimental results are plotted in FIG. 10B. It is clear that the calculation predicts the oven exposure results well. It is noted that the magnitude of the thermal runaway (for the 155° C. oven test) is weaker in the calculation because only the first cathode/electrolyte exotherm is included in the model.

Figures 11A, 11B:
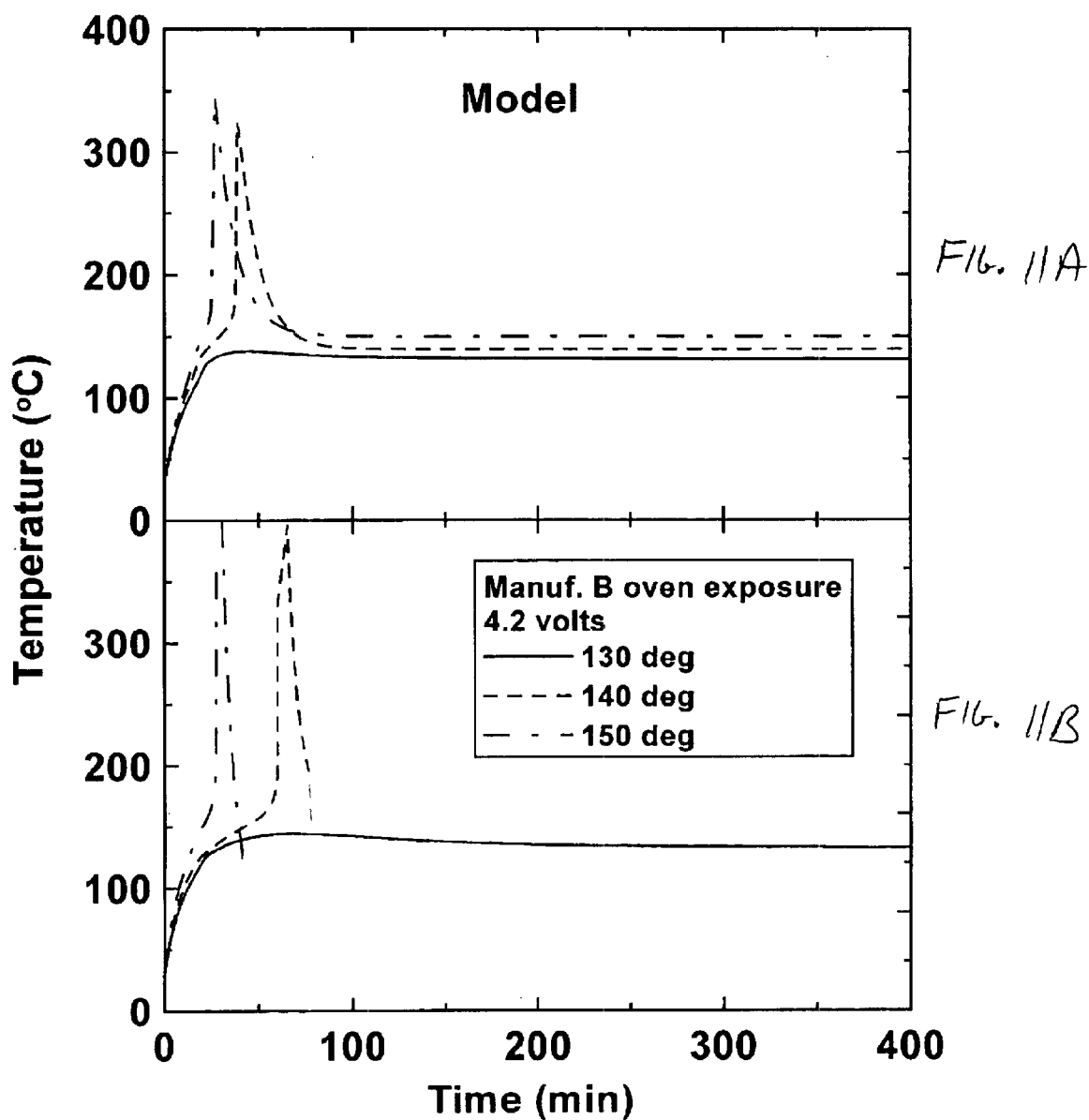
FIGS. 11A–11B are temperature vs. time graphs illustrating a comparison of the calculated and measured oven-exposure profiles for cells from a second manufacturer (Manufacturer B) according to an embodiment of the present invention.

Oven exposure experiments were also made on 17670 cells from manufacturer B. Power functions were not developed for the electrode materials used in those cells. FIG. 11B shows the oven exposure test results. Clearly, the cells made by manufacturer B are less stable than those made by manufacturer A. If power functions for the materials used by manufacturer B were developed, the results in FIG. 11B could be predicted. On the other hand, attempting to match the results in FIG. 11B, such as by varying the parameters of the power functions, allows reasonable estimates to be made. FIG. 11A shows calculations to simulate the experiments in FIG. 11B. Only parameters of the cathode power functions were changed from the values listed in Table 2 above. The parameter H was increased to 450 J/g and y was increased to 1.5×10$^{17}$ min$^{-1}$. Using this approximate set of parameters, predictions about the safety of other cell sizes and shapes could be made.

EXAMPLE #6

Figure 12:
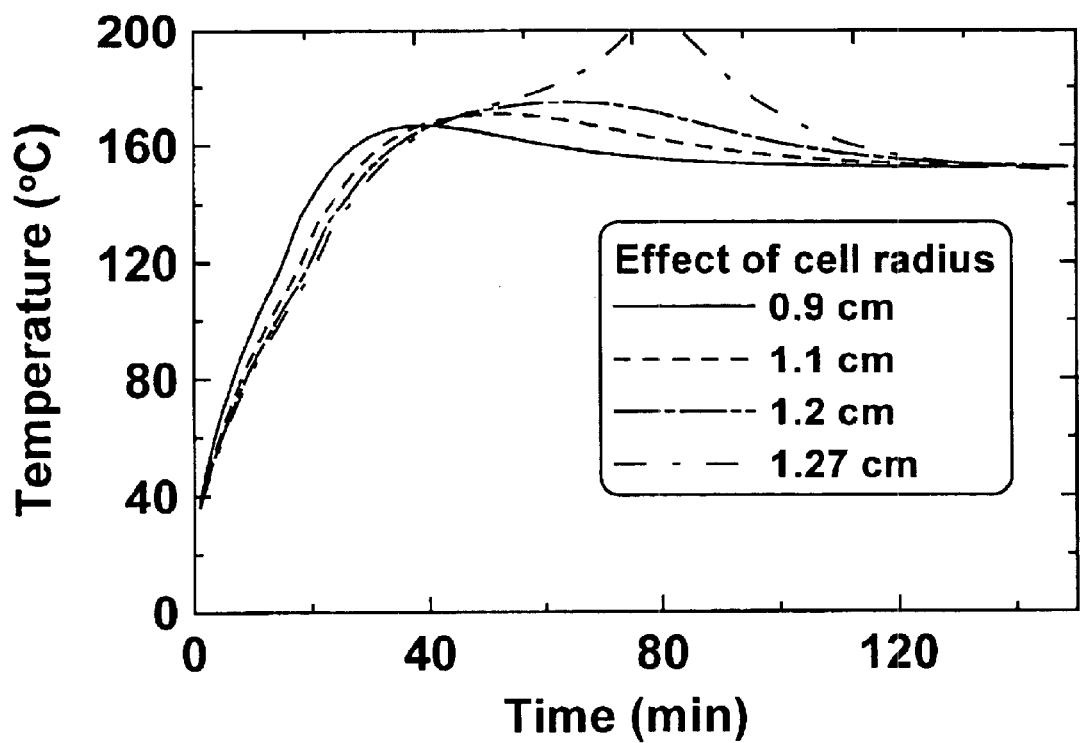
FIG. 12 is a temperature vs. time graph illustrating calculated oven exposure profiles (150° C.) as a function of cell radius for cells using the parameters in Table 2 below.

Once confidence in the method is achieved, it is then possible to predict oven exposure results for cells of different diameters. FIG. 12, for example, shows predictions for oven exposure tests at 150° C. for cells from manufacturer A as a function of cell radius. Clearly, it is evident that decreasing the cell radius improves the thermal stability of the cell. A critical radius of 1.2 cm is found for cells that can pass extended exposure to 150° C. It is appreciated that determining the critical radius for a particular cell design using the modeling approach of the present invention is significantly less complex, less time consuming, and less costly than assembling many cells of different diameters and then testing the assembled cells. Similar predictions may be made for planar cells without ever having to build planar prototype cells.

The methodology described hereinabove for obtaining power functions and using same to model cell and battery level behavior in response to user prescribed thermal conditions and/or thermal abuse conditions may also be used to predict the response of such cells an d batteries to other forms of environmental conditions/abuse, such as mechanical and electrical abuse. The discussion provided thus far has focused on how power functions determined by accelerating rate calorimetry or differential scanning calorimetry may be used to predict the behavior of lithium-ion batteries in the oven exposure test. Power functions may also be used to model cell/battery behavior when subjected to an overcharge test, a short-circuit test, and a nail penetration test, for example.

In order to predict the response of cylindrical and planar cells to overcharge conditions, one only needs to add the electrically generated power per unit volume, $P_e$, to the oven exposure scenario, and set the environmental temperature to a temperature near room temperature. The electrically generated power may be approximated by multiplying the current by the cell overvoltage. The cell overvoltage is defined as the terminal voltage under load minus the open circuit voltage at the nominal top of charge. For example, if a 3 A charging current is forced through a cell with a 4 V overvoltage, then 12 W of electrical power is dissipated in the cell. This value of electrical power is divided by the cell volume to arrive at $P_e$. Calculations are then straightforward.

According to one embodiment of an overcharge test modeling approach, a cell is charged for several times its rated capacity using a current that would normally give a full charge in a duration of time defined by 1/C of an hour. Normally C is selected to be 1 or 3 in this test. Once the normal chemistry of the charge process has been completed, the cell voltage rises to a value, V, which can be a volt or more above the open circuit voltage, $V_c$, of the charged cell. The electrical power dissipated in the cell is then approximated by the equation $P=I(V-V_c)$. This causes heating of the cell above ambient temperature.

Eventually, the cell will reach a temperature where chemically generated power from the electrodes becomes significant. This can be calculated using the above-described power function approach. In order to make reasonable predictions of cell behavior during overcharge, a reasonable understanding of the variation of cell voltage with respect to time and current during the overcharge process is required. Also required is a knowledge of the amount of metallic lithium electroplated on the negative electrode during overcharge. For most lithium-ion cells, this is a concern.

Power functions for negative electrodes containing plated metallic lithium would need to be developed in this case. Further, knowledge of the effect of electrolyte decomposition products at the positive electrode on the positive electrode power functions is required. Modeling of cell/battery behavior in response to an overcharge condition may be enhanced by performing experiments to first determine the various unknowns, which would otherwise be obtained using reasonable estimations and refinement of such estimations during the modeling exercise.

In accordance with one embodiment of a short-circuit test modeling approach, a fully charged cell is equilibrated at some temperature, T. The cell is then short-circuited externally through a low impedance connection. Current flows and power is dissipated within the cell due to its internal impedance (I$^2$R). This impedance varies as a function of temperature. The temperature of the cell rises, and the state of charge of the electrodes changes as the electrodes discharge. Once the cell reaches the separator shutdown point (e.g., near 130° C. for a lithium-ion cell), the current flow stops and heat generated within the cell may be predicted by the power functions that correspond to the cell's present state of charge. Newton's law of cooling may be used to estimate heat transfer to the environment.

Modeling of a short-circuit test is relatively straightforward, assuming that a good model for cell impedance as a function of temperature and state of charge is employed. Measurements could determine this accurately.

Straightforward modeling of the short-circuit test also assumes that the power functions over the range of the state of charge of the cell "traversed" during the short-circuit are known. This would require measurements of power functions at several lithium concentrations in both the positive and negative electrodes.

In accordance with one embodiment of a nail penetration modeling approach, a nail having a point of a specified radius is forced into a cell at a specified rate. This causes an internal short-circuit of the cell. This results in intense heating at the site of the short-circuit which can lead to thermal runaway. Normally, cells are fully charged before the test. As such, power functions for fully charged materials are needed.

Cells filled with solvent only (not electrolyte) may be characterized by nail penetration. The resistance between the cell electrodes as a function of time may be measured as the nail is inserted. Once this resistance is known, then the short-circuit current that flows, as the nail is inserted in an electrolyte-filled cell, may be estimated.

The electrically generated power, $V^2/R$, is dissipated in the vicinity of the point of the nail. This causes local heating. The heat flow from this point may be treated with the above-described heat equation, preferably using a three-dimensional form with small spatial grid. As the temperature rises, the chemically generated power may be estimated using the power functions and hence a complete description of the nail penetration process may be obtained.

A cell/battery behavior modeling approach which is based on power functions developed in accordance with the principles of the present invention may be implemented using modeling software running on a computer-based processing facility, such as a workstation, personal computer or other microprocessor-based computing system.

In accordance with one embodiment, a software program provides for user-interactive cell/battery behavior modeling using a WINDOWS-like interface. FIGS. 13–20 are screen images of such an interface according to an embodiment of the present invention. In general terms, the user-interface allows the battery designer to create "virtual" cells of any shape and size and to predict the response of the virtual cells to user-specified conditions of thermal, electrical, and mechanical abuse. The user-interface allows the battery designer to load and modify anode, cathode, battery, and environmental parameters, and to graphically display the predicted behavior of the anode, cathode, and battery based on the loaded/modified parameters. As such, incremental changes may be made to the various virtual cell parameters to refine the behavior of a particular battery design.

The cell/battery modeling software of the present invention provides for accurate mathematical modeling of virtual cell behavior based on power functions developed from accelerating rate calorimetry or differential scanning calorimetry experiments on small quantities of particular electrode/electrolyte materials prepared in lab cells. One skilled in the art will immediately appreciate the significant cost and time saving advantages of a cell/battery design and modeling approach which requires the availability of only small amounts of sample electrode/electrolyte materials, and one in which cell prototype building and testing is completely eliminated.

The cell/battery design and modeling approach of the present invention is particularly useful when developing "new" or advanced electrode/electrolyte materials which may be produced in small quantities but would be cost or time prohibitive to produce in large quantities. Since the power functions needed to fully characterize cell-level/battery-level behavior for a new electrode/electrolyte material may be developed from calorimetry experiments on small quantities of the new material, it is believed that the cell modeling system and software of the present invention may significantly assist in the research and development of advanced cell technologies.

According to one embodiment, the behavioral data of a known battery (e.g., a commercially available 18650 lithium-ion battery) when subjected to a thermal abuse test may be made available to the battery designer for purposes of providing a performance baseline or standard for a known cell technology. For example, experimentally derived temperature-time data for any number of known battery or cell types may be stored and accessed by the cell designer. Assuming that a "new" battery material has been developed and power functions obtained from a small sample of same in a manner discussed previously, the modeling software of the present invention may be used to plot temperature-time data for an 18650 battery having the new battery material. This plot may be compared against that of one or more known 18650 cell types to determine if the "new" battery is as safe, less safe, or safer than the known cell. It is understood that data that characterizes known cells is not necessary to the present invention, but may be used to enhance the process of evaluating new and different cell chemistries and configurations in relation to known cell designs.

Figure 13:
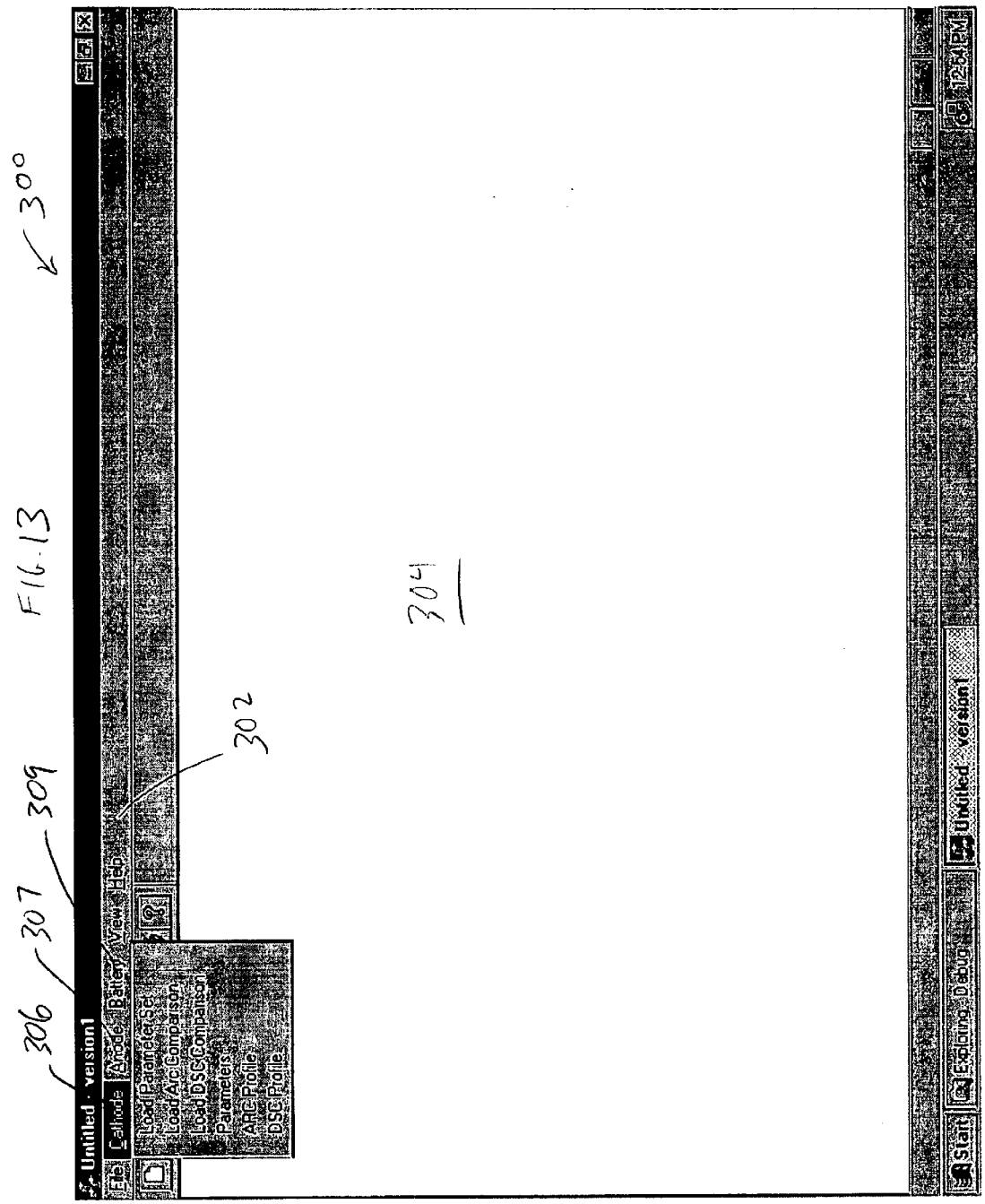
FIG. 13 is a depiction of a user-interface screen presented on a computer system display which provides for user interaction with a cell/battery modeling program in accordance with the principles of the present invention.

Referring now to FIG. 13, a main screen 300 of a user-interface according to an embodiment of the present invention includes a main menu bar 302 and a template region 304. The main menu bar 302 includes a number of control buttons, including, in particular, a Cathode button 306, an Anode button 307, and a Battery button 309. Each of the Cathode, Anode, and Battery buttons 306, 307, 309, when actuated, provides for the selection of additional particularized functions. As shown in FIG. 13, the Cathode button 306 has been activated which allows for additional selections associated with modeling the cathode of a virtual cell.

Figure 14:
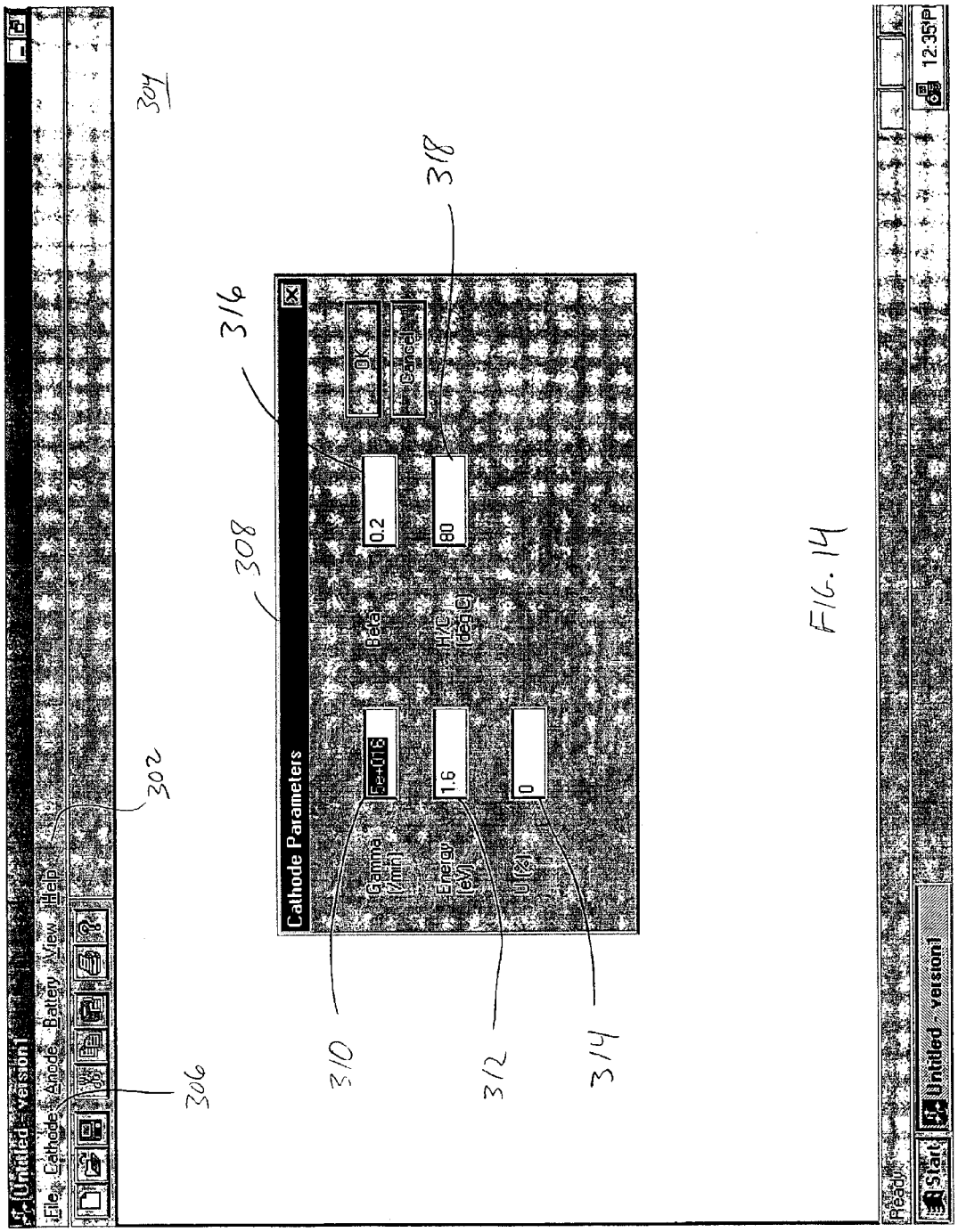
FIG. 14 is a depiction of a user-interface screen presented on a computer system display which provides for user input and adjustment to various cathode parameters in accordance with a cell/battery modeling program embodiment of the present invention.

FIG. 14 depicts an input screen or dialog box 308 that is activated by selection of the Parameters button made available by actuation of the Cathode button 306 from the main menu bar 302, as is shown in FIG. 13. Activation of the Parameters button results in presentation of a Cathode Parameters dialog box 308, which provides for loading and adjusting of various cathode specific parameters by the battery designer. The Cathode Parameters dialog box 308 may be accessed via another route. Activation of the Load Parameters Set button, also shown in FIG. 13, brings up an Open File dialog box, from which the user selects a file. Upon selecting a file, the Cathode Parameters dialog box 308 is presented, which provides for loading and adjusting of various cathode specific parameters associated with the selected file.

An input field 310 is provided for entering a value for Gamma, γ, which represents a frequency factor expressed in terms of minutes$^{-1}$. An input field 312 is provided for entering a value for the activation energy, $E_a$, which is expressed in terms of electron volts (eV). The parameter u, which is the dimensional fractional (i.e., percentage) degree of conversion, may be entered using input field 314. An input field 316 is provided for entering a value for Beta, β, which represents the dimensionless parameter of autocatalysis. The value of $h/C'_{tot}$ may also be entered using input field 318, where $h/C'_{tot}$ represents the ratio of the total heat (h) evolved by the sample due to the reaction and the total heat capacity ($C'_{tot}$) of the reactant and the sample bomb expressed in terms of ° C.

Figure 15:
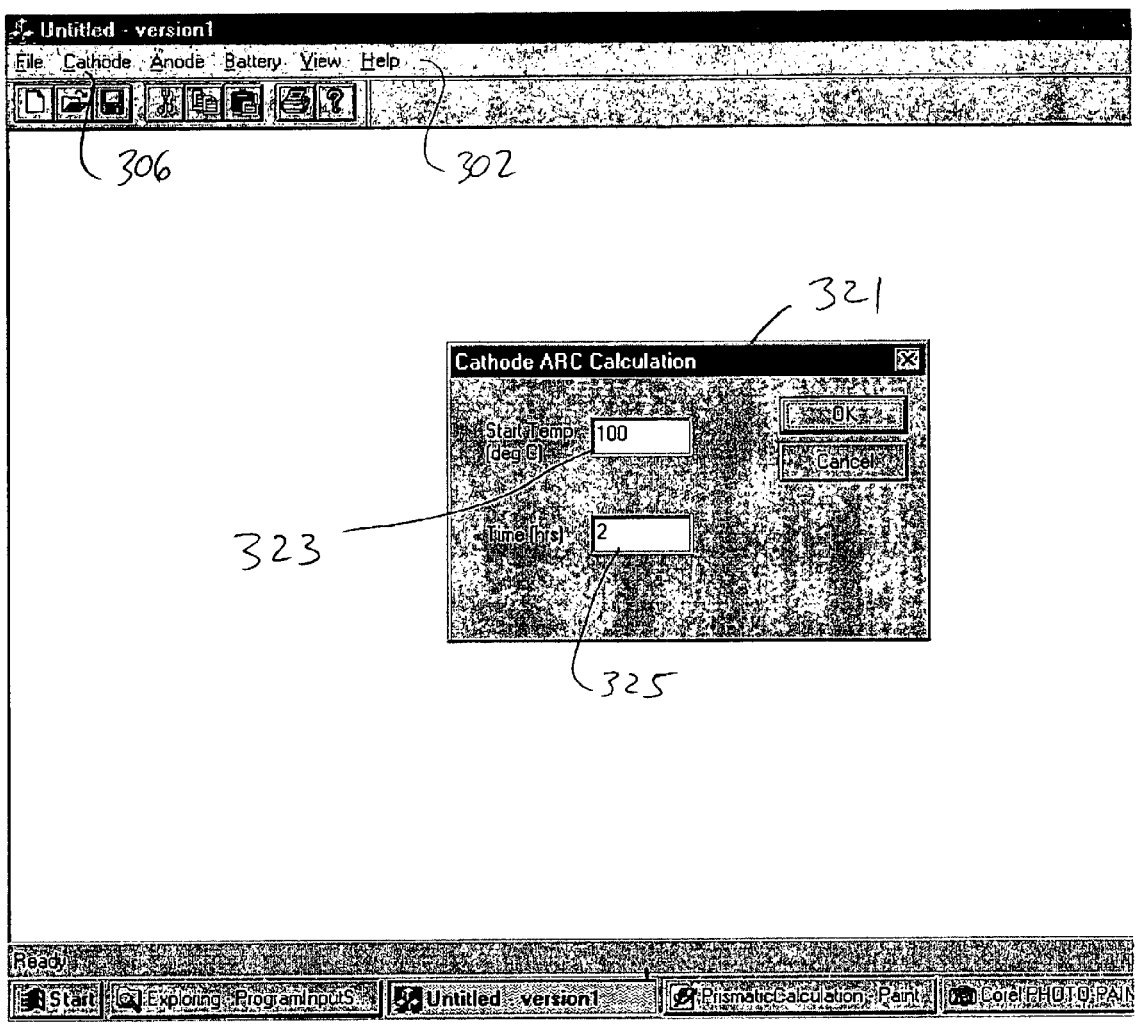
FIG. 15 is a depiction of a user-interface screen presented on a computer system display which provides for user input and adjustment to various data concerning accelerating rate calorimetry cathode calculations in accordance with a cell/battery modeling program embodiment of the present invention.
Figure 16:
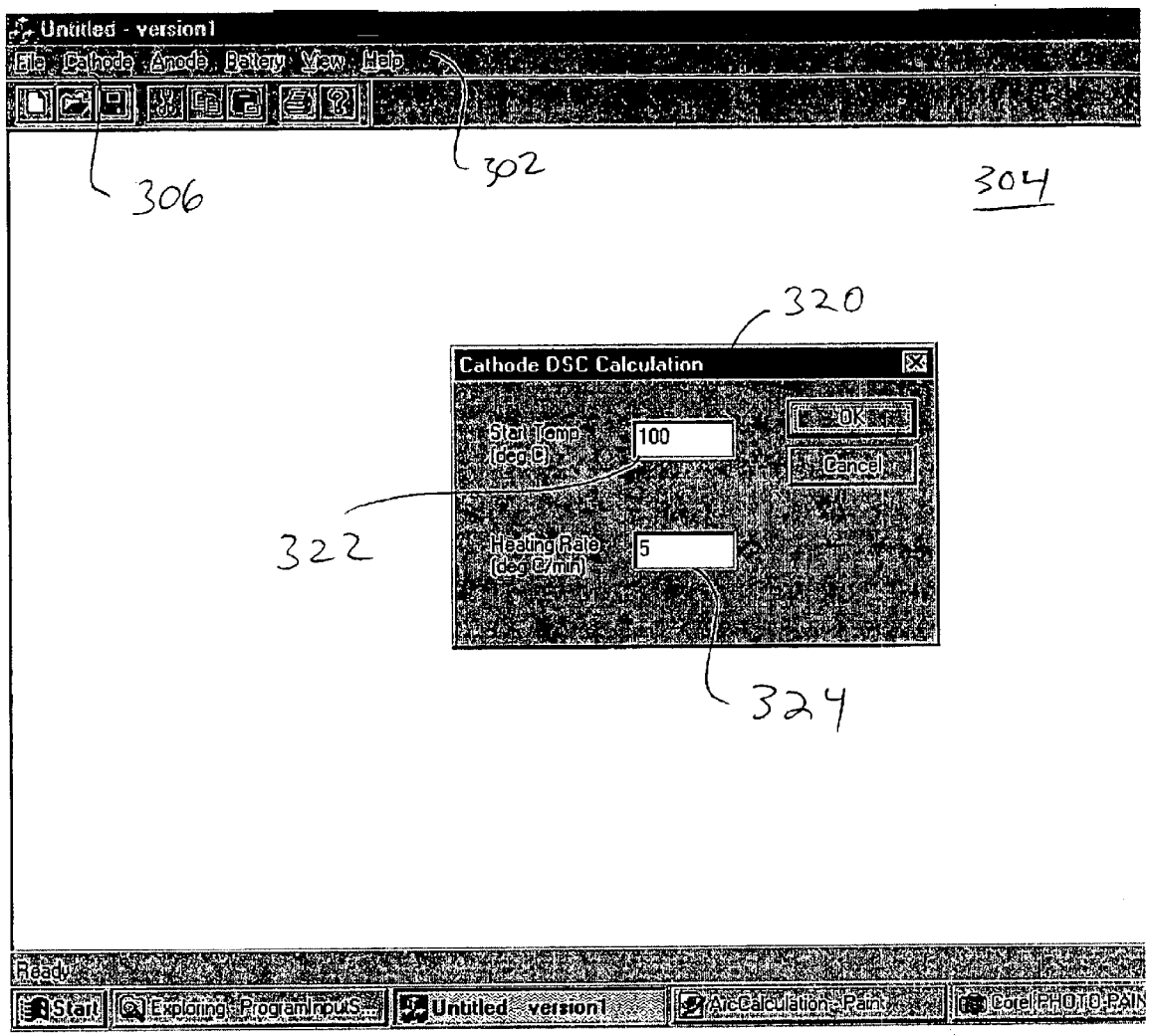
FIG. 16 is a depiction of a user-interface screen presented on a computer system display which provides for user input and adjustment to various data concerning differential scanning calorimetry cathode calculations in accordance with a cell/battery modeling program embodiment of the present invention.

FIGS. 15 and 16 show dialog boxes 321 and 320 for entering parameters affecting the cathode calculations using accelerating rate calorimetry and differential scanning calorimetry techniques, respectively. Each of the dialog boxes 321 and 320 provided a Starting Temperature input field 323, 322, expressed in terms of ° C. The dialog box 321 for inputting cathode accelerating rate calorimetry calculation parameters includes a Time input field 325, expressed in terms of hours. The dialog box 320 for inputting cathode differential scanning calorimetry calculation parameters includes a Heating Rate input field 324, expressed in terms of ° C. per minute.

Figure 17:
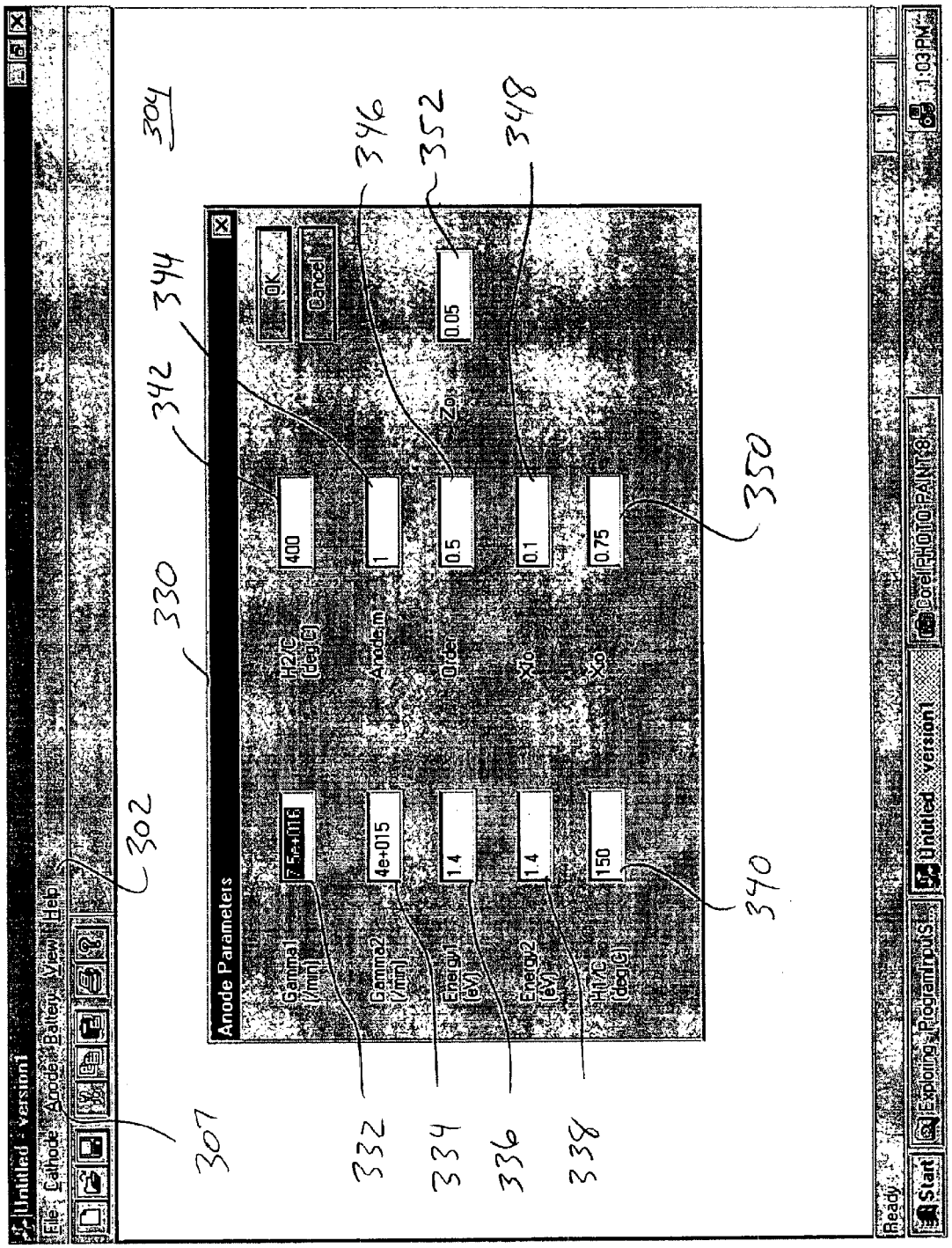
FIG. 17 is a depiction of a user-interface screen presented on a computer system display which provides for user input and adjustment to various anode parameters in accordance with a cell/battery modeling program embodiment of the present invention.

FIG. 17 shows an Anode Parameters dialog box 330 which is activated by selection of the Parameters button made available upon actuation of the Anode button 307 from the main menu bar 302; Activation of the Parameters button results in the presentation of the Anode Parameters dialog box 330, which provides for loading and adjusting of various anode specific parameters by the battery designer. The Anode Parameters dialog box 330 may be accessed via a different route. Activation of the Load Parameters Set button, which becomes available upon actuating the Anode button 307 shown in FIG. 13, brings up an Open File dialog box from which the user selects a file. Upon selecting a file, the Anode Parameters dialog box 330 is presented, which provides for loading and adjusting of various anode specific parameters associated with the selected file.

An input field 332 is provided for entering a value for Gamma-1, $\gamma_1$, and input field 334 provides for entering of a value for Gamma-2, $\gamma_1$, which respectively represent frequency factors expressed in terms of minutes$^{-1}$. Input fields 336 and 338 provide for entering a value for activation energy parameters, $E_1$ and $E_2$, each of which is expressed in terms of electron volts (eV). The value of $h_1/C'_{tot}$ and $h_2/C'_{tot}$ may be entered using input fields 340 and 342, where the terms $h_1/C'_{tot}$ and $h_2/C'_{tot}$ have units as described previously in Example #4 hereinabove.

Anode Parameters dialog box 330 further includes an Anode m input field 344, where Anode m represents the reaction order for the reaction of type 1 to type 3 lithium. An Order input field 356 allows the designer to enter an Order value, which represents the reaction order for the reaction of type 2 to type 3 lithium. An Xfo input field 348 is provided to allow entering of a value for the anode parameter Xfo, which represents the term $x_{2o}$ having units as described previously in Example #4 hereinabove. The anode parameter Xio, which represents the term $x_{1o}$ having units as described previously in Example #4 hereinabove, may be entered using xio input field 350. A Zo input field 352 provides for entering of a value for the anode parameter Zo, which represents the term $x_{3o}$ having units as described previously in Example #4 hereinabove.

Figure 18:
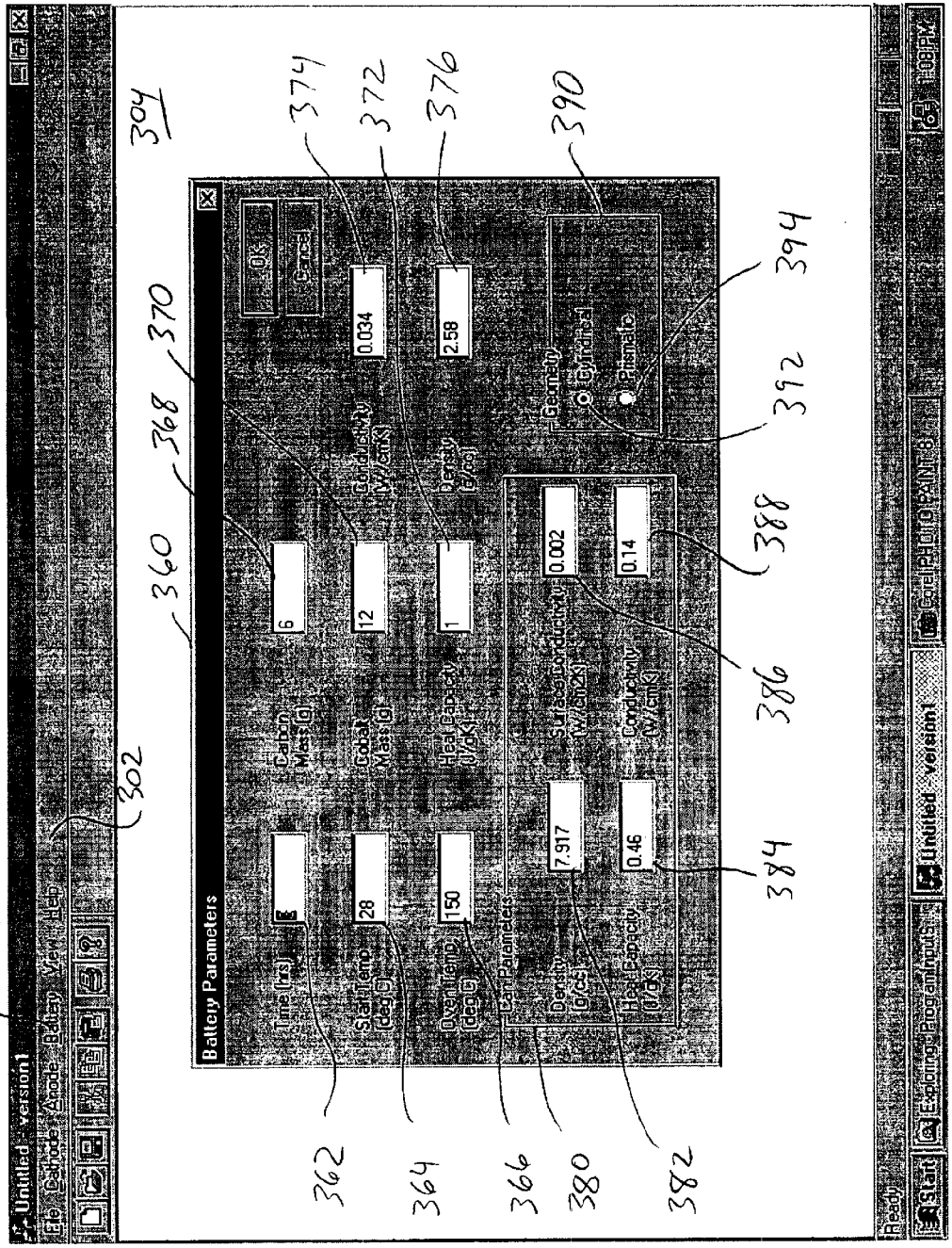
FIG. 18 is a depiction of a user-interface screen presented on a computer system display which provides for user input and adjustment to various battery parameters in accordance with a cell/battery modeling program embodiment of the present invention.

FIG. 18 shows a dialog box 360 which is activated by selection of the Battery button 309 from the main menu bar 302. A Battery Parameters dialog box 360 provides for loading and adjusting of various battery level parameters by the battery designer. Input fields 362 and 364 provide for entering of Time (hrs) and Start Temperature ° C.) values, respectively. An Oven Temperature field 366 allows the designer to input a temperature (° C.) of the oven into which the cell will be placed in accordance with an oven exposure test. It is noted that the cell is initially at the Start Temperature.

Mass input fields 368 and 370 provide for the input of mass values (g) for the anode and cathode, respectively. In FIG. 18, the Mass input fields 368 and 370 are specific for carbon and cobalt based electrodes, respectively, for a virtual lithium-ion battery. Values for battery heat capacity (J/gK), thermal conductivity (W/cmK), and density (g/cc) may be entered using input fields 372, 374, and 376, respectively. The Battery Parameters dialog box 360 further includes a Can Parameters region 380 which allows for the entering of various data that characterize the can or protective enclosure of the virtual battery. Can Parameters region 380 includes input fields 382, 384, 386, and 388 for entering values for can density (g/cc), heat capacity (J/gK), can surface heat conductivity (W/cm$^2$K), and can bulk thermal conductivity (W/cmK), respectively.

The Battery Parameters dialog box 360 further includes a Battery Geometry region 390 which provides for the selection of several different virtual battery geometries. In the embodiment depicted in FIG. 18, a designer may activate a Cylindrical Geometry button 392 or a Prismatic Geometry button 394.

Figure 19:
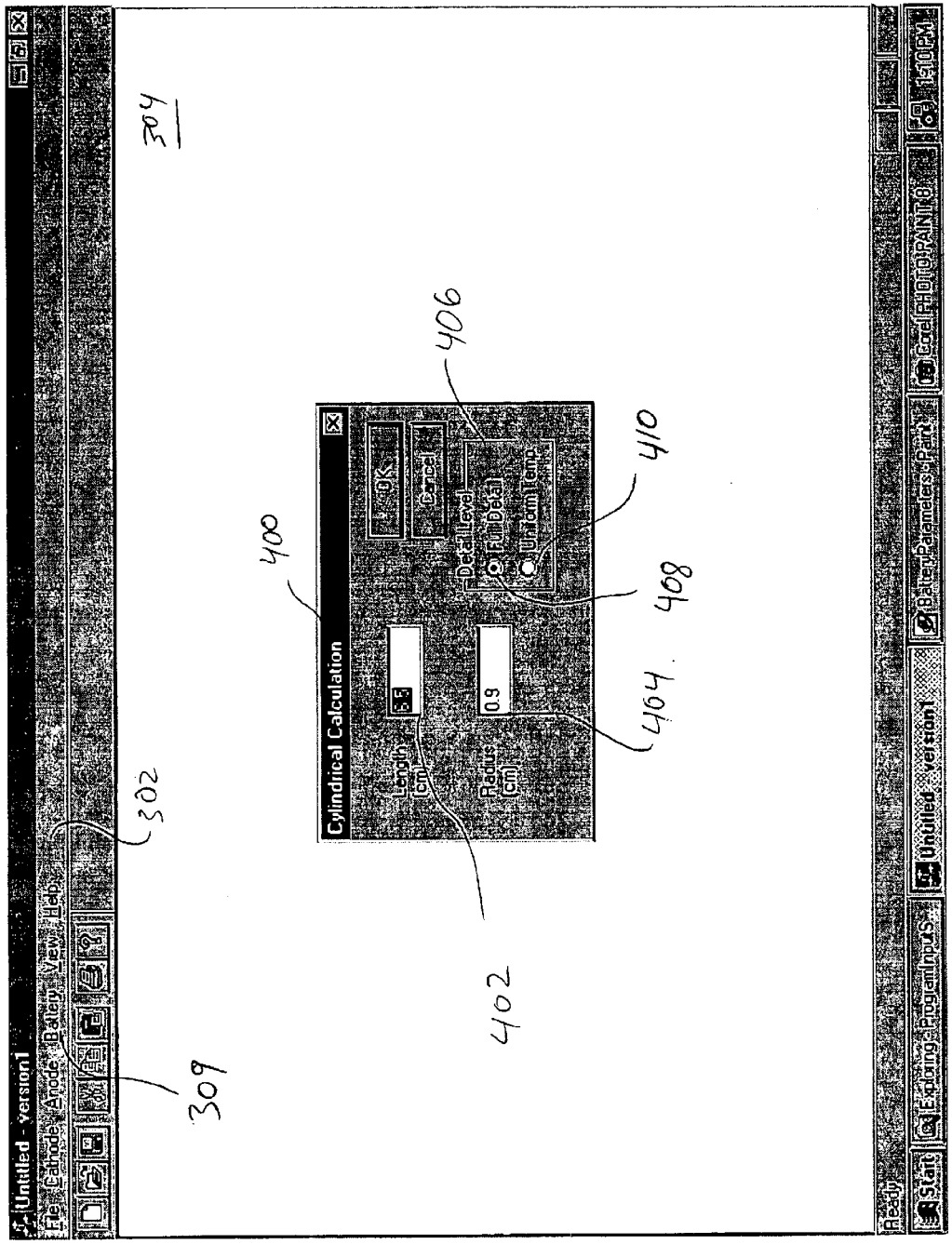
FIG. 19 is a depiction of a user-interface screen presented on a computer system display which provides for user input and adjustment to various parameters of a battery having a cylindrical configuration in accordance with a cell/battery modeling program embodiment of the present invention.

FIG. 19 shows a Cylindrical Calculation dialog box 400 which is presented to the designer in response to activating the Cylindrical Geometry button 392 provided in the Battery Geometry region 390. The designer may enter can length (cm) and radius (cm) values using Length and Radius input fields 402 and 404, respectively.

The Cylindrical Calculation dialog box 400 further includes a Detail Level region 406 which permits the designer to activate a Full Detail button 408 and a Uniform Temperature button 410. Activation of the Full Detail button 408 results in a calculation that assumes that the temperature within the virtual cell varies with radius, as given by the above-described heat equation. Implemented on a PC equipped with a 266 MHz Pentium II processor, the Full Detail computation takes several minutes to complete.

Activation of the Uniform Temperature button 410 results in a calculation that assumes that the temperature within the virtual cell is uniform (i.e., no radius dependence). This calculation is approximate, but is completed in seconds. The approximation is, however, reasonably accurate. Simulations have demonstrated that the typical core-can temperature difference is only a few degrees C, even during thermal runaway.

Figure 20:
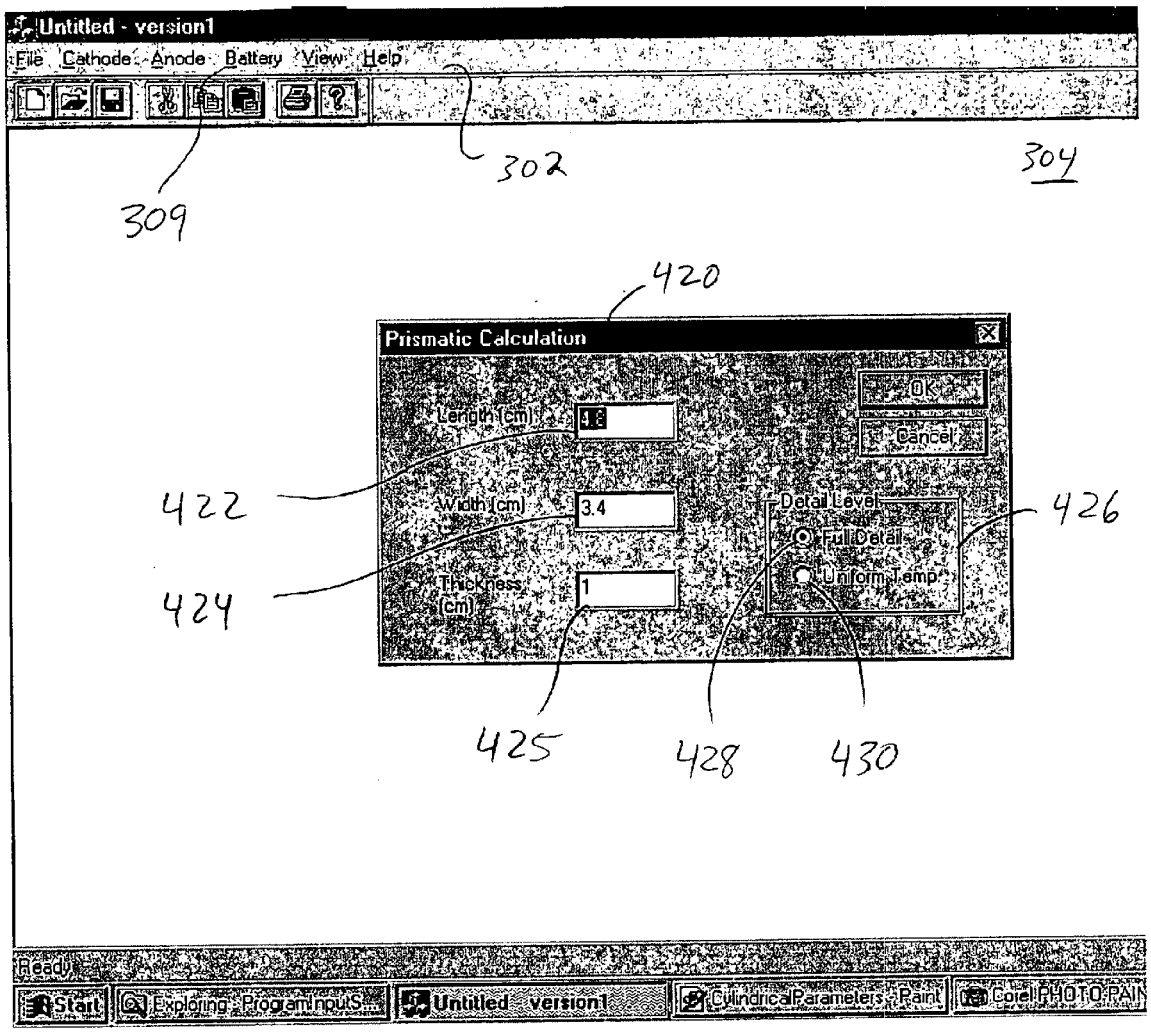
FIG. 20 is a depiction of a user-interface screen presented on a computer system display which provides for user input and adjustment to various parameters of a battery having a prismatic configuration in accordance with a cell/battery modeling program embodiment of the present invention.

FIG. 20 shows a Prismatic Calculation dialog box 420 which is presented to the designer in response to activating the Prismatic Geometry button 394 provided in the Battery Geometry region 390 shown in FIG. 18. The designer may enter can length (cm), width (cm), and thickness (cm) values using Length, Width, and Thickness input fields 422, 424, and 425, respectively. The Prismatic Calculation dialog box 420 also includes a Detail Level region 426 which permits the designer to activate Full Detail and Uniform Temperature buttons 428 and 430.

Activation of the Full Detail button 428 results in a calculation that assumes that the temperature within the virtual cell varies with thickness, as given by the above-described heat equation. As in the case of a cylindrical cell geometry, activation of the Uniform Temperature button 430 results in a calculation that assumes that the temperature within the virtual cell is uniform (i.e., no thickness dependence).

A computer assisted method for predicting the response of electrochemical cells to thermal, electrical, and/or mechanical abuse according to the present invention may thus be effected, for example, by a processor implementing a sequence of machine-readable instructions. In the embodiment shown in FIG. 1, for example, a processor 121 (e.g., PC) is communicatively coupled to the calorimeter 100, such as by a wired or wireless link 129. The processor 121 includes a memory 123 and is capable of storing/reading data to/from portable memory media 127. A user interface 125, which includes a display, is coupled to the processor 121. Machine-readable instructions may reside in various types of signal-bearing media. In this respect, another embodiment of the present invention concerns a programmed product which includes a signal-bearing medium embodying a program of machine-readable instructions, executable by a digital processor to perform method steps to effect cell modeling and behavior prediction procedures of the present invention. The signal-bearing media may include, for example, random access memory (RAM) provided within, or otherwise coupled to, the processor (e.g., memory 123).

The foregoing description of the various embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What we claim is:

1. A method of characterizing electrochemical cell components, comprising:

preparing a sample of an electrode material in contact with an electrolyte;

obtaining self-heating data, power-temperature data or power-time data for the sample using a calorimetry technique; and developing a power function for the sample using the self-heating, power-temperature or power-time data, the power function representative of thermal power per unit mass of the sample as a function of temperature and amount of reactant remaining from a reaction of the electrode material and electrolyte of the sample.

2. The method of claim 1, wherein preparing the sample comprises preparing the sample using less than about 100 grams of the electrode material.

3. The method of claim 1, wherein preparing the sample comprises preparing the sample using between about 1 and about 10 grams of the electrode material.

4. The method of claim 1, wherein preparing the sample comprises preparing the sample using between about 1 milligram and about 1 gram of the electrode material.

5. The method of claim 1, wherein the electrode material comprises cathode material.

6. The method of claim 1, wherein the electrode material comprises anode material.

7. The method of claim 1, wherein the electrode material comprises lithium.

8. The method of claim 1, wherein obtaining the self-heating data comprises obtaining temperature versus time data of the sample during reaction under substantially adiabatic conditions.

9. The method of claim 1, wherein using the calorimetry technique comprises using an accelerating rate calorimetry technique.

10. The method of claim 1, wherein using the calorimetry technique comprises using a differential scanning calorimetry technique.

11. A method of characterizing electrochemical cell components, comprising:

preparing a first sample of a cathode material in contact with an electrolyte;

preparing a second sample of an anode material in contact with the electrolyte;

obtaining first and second self-heating, power-temperature or power-time data for the first and second samples, respectively, using a calorimetry technique; and developing a first power function for the first sample and a second power function for the second sample using the first and second self-heating, power-temperature or power-time data, respectively, the first power function characterizing a reaction between the cathode material and the electrolyte in terms of thermal power per unit mass of the cathode sample material, and the second power function characterizing a reaction between the anode material and the electrolyte in terms of thermal power per unit mass of the anode sample material.

12. The method of claim 11, wherein preparing the first sample comprises preparing the first sample using less than about 100 grams of the cathode material and preparing the second sample comprises preparing the second sample using less than about 100 grams of the anode material.

13. The method of claim 11, wherein preparing the first sample comprises preparing the first sample using between about 1 and about 10 grams of the cathode material and preparing the second sample comprises preparing the second sample using between about 1 and about 10 grams of the anode material.

14. The method of claim 11, wherein preparing the first sample comprises preparing the first sample using between about 1 milligram and about 1 gram of the cathode material and preparing the second sample comprises preparing the second sample using between about 1 milligram and about 1 gram of the anode material.

15. The method of claim 11, wherein the cathode and anode material each comprises lithium.

16. The method of claim 11, wherein obtaining the first and second self-heating data comprises obtaining temperature versus time data of the first and second samples during reaction under substantially adiabatic conditions, respectively.

17. The method of claim 11, wherein using the calorimetry technique comprises using an accelerating rate calorimetry technique.

18. The method of claim 11, wherein using the calorimetry technique comprises using a differential scanning calorimetry technique.

19. A method of characterizing an electrochemical cell, comprising:

defining one or more physical parameters of the electrochemical cell;

providing a first power function characterizing a reaction between a cathode and an electrolyte in terms of thermal power per unit mass of cathode material;

providing a second power function characterizing a reaction between an anode and the electrolyte in terms of thermal power per unit mass of anode material; and predicting, using the first and second power functions and the physical parameters of the electrochemical cell, a response of the cell to a specified operating condition.

20. The method of claim 19, wherein the method is implemented using a computer and user-interface coupled to the computer.

21. The method of claim 19, wherein:

defining one or more physical parameters of the cell further comprises adjusting the physical parameters of the cell; and predicting the response of the cell further comprises predicting the response of the cell using the first and second power functions and the adjusted physical parameters of the cell.

22. The method of claim 19, wherein defining one or more physical parameters of the cell further comprises receiving user input data representative of physical parameters of the cell.

23. The method of claim 22, wherein receiving user input data further comprises:
presenting to a user an input field corresponding to each physical parameter of the cell; and
receiving input data from the user in each of the input fields.

24. The method of claim 19, wherein defining one or more physical parameters of the cell further comprises receiving physical parameters of the cell electronically.

25. The method of claim 19, wherein defining one or more physical parameters of the cell further comprises receiving physical parameters of the cell from an external host processor.

26. The method of claim 19, wherein defining one or more physical parameters of the cell further comprises defining one or more physical parameters for each of an anode and a cathode of the cell.

27. The method of claim 26, further wherein:
defining physical parameters for each of the anode and cathode of the cell further comprises adjusting the physical parameters of one or both of the anode and cathode; and
predicting the response of the cell further comprises predicting the response of the cell using the first and second power functions and the adjusted physical parameters of one or both of the anode and cathode.

28. The method of claim 19, wherein the specified operating condition comprises a condition of constant or varying ambient temperature.

29. The method of claim 19, wherein the specified operating condition comprises a condition of a constant or varying current applied to the cell.

30. The method of claim 19, wherein the specified operating condition comprises a condition of an external short-circuit connected to the cell.

31. The method of claim 19, wherein the specified operating condition comprises a condition of a short-circuit internal to the cell.

32. A system for characterizing an electrochemical cell, comprising:
a processor;
a user-interface, coupled to the processor, comprising an input device operable by a user for entering one or more physical parameters of the electrochemical cell; and
memory, coupled to the processor, that stores a cathode power function characterizing a reaction between a cathode and an electrolyte in terms of thermal power per unit mass of cathode material and further stores an anode power function characterizing a reaction between an anode and the electrolyte in terms of thermal power per unit mass of anode material, the processor computing a response of an electrochemical cell to a specified operating condition using the cathode and anode power functions and the physical parameters of the electrochemical cell.

33. The system of claim 32, wherein:
the input device is operable by the user to enter physical parameters of an anode and a cathode of the cell; and
the processor computes the response of the electrochemical cell to the specified operating condition using the cathode and anode power functions and the entered physical parameters of the anode and cathode of the electrochemical cell.

34. The system of claim 32, wherein:
the input device is operable by the user to adjust physical parameters of the cell; and
the processor computes the response of the electrochemical cell to the specified operating condition using the cathode and anode power functions and the adjusted physical parameters of the electrochemical cell.

35. The system of claim 32, wherein:
the input device is operable by the user to adjust physical parameters of an anode and a cathode of the cell; and
the processor computes the response of the electrochemical cell to the specified operating condition using the cathode and anode power functions and the adjusted physical parameters of the anode and cathode of the electrochemical cell.

36. The system of claim 32, wherein the user-interface comprises a display, and the input device is operable by the user for entering physical parameters of the electrochemical cell into input fields presented on the display.

37. The system of claim 32, wherein the user-interface comprises a display, and the input device is operable by the user for entering physical parameters of an anode and a cathode of the electrochemical cell into input fields presented on the display.

38. The system of claim 32, wherein the memory that stores the anode and cathode power functions is partially or completely situated remotely from the processor.

39. The system of claim 32, further comprising a calorimeter system coupled to the processor.

40. The system of claim 32, wherein the calorimeter system comprises an accelerating rate calorimeter or a differential scanning calorimeter.

41. A method of characterizing electrochemical cell components, comprising:
defining one or more physical parameters of an electrochemical cell;
characterizing a reaction between a cathode and an electrolyte in terms of thermal power per unit mass of cathode material by defining a first power function;
characterizing a reaction between an anode and the electrolyte in terms of thermal power per unit mass of anode material by defining a second power function; and
predicting, using the first and second power functions and the physical parameters of the electrochemical cell, a response of the cell to a specified operating condition.

42. The method of claim 41, wherein characterizing the respective cathode/electrolyte and anode/electrolyte reactions comprises modeling the respective reactions assuming an autocatalytic reaction mechanism.

43. The method of claim 41, wherein the first power function, $P_c$, associated with the cathode/electrolyte reaction is given by the following equations:

$$\frac{du}{dt} = k(1-u)(\beta + u^{0.5})$$

$$\frac{dT}{dt} = \frac{h}{C'_{tot}} * \frac{du}{dt}$$

$P_c = H du/dt$ where, u represents a dimensionless fractional degree of conversion, k represents a reaction rate constant defined by $k=\gamma \exp(-E_a/k_b T)$, $\gamma$ represents a frequency factor expressed in terms of minutes$^{-1}$, $E_a$ represents activation energy, $k_b$ represents Boltzmann's constant, T represents a temperature of the cell, $\beta$ represents a dimensionless parameter of autocatalysis, h represents total heat which can be evolved by a sample of cathode material during reaction expressed in terms of Joules, $C'_{tot}$ represents a total heat capacity of the reactant and a sample calorimeter bomb expressed in terms of J/K, and H represent total heat generated by the cathode/electrolyte reaction per gram of cathode material.

44. The method of claim 41, wherein the second power function, $P_a$, associated with the anode/electrolyte reaction is given by:

$$P_a = H_2 \left| \frac{dx_2}{dt} \right| + H_1 \left| \frac{dx_1}{dt} \right|$$

where, $$\frac{dx_2}{dt} = -\gamma_2 \exp^{-E_2/k_b T} x_2^{0.5}$$

$$\frac{dx_1}{dt} = -\gamma_1 \exp^{-E_1/k_b T} x_1 \exp^{-((x_{3o}+x_{2o})+f(x_{1o}-x_1))/(x_{3o}+x_{2o})} \text{ and}$$

$$\frac{dx_3}{dt} = -\frac{dx_1}{dt} - \frac{dx_2}{dt}$$

further where, $x_1$ represents an amount of type 1 lithium measured as x in $Li_x C_6$, $x_2$ is an amount of type 2 lithium, measured per six carbons, and $x_3$ is an amount of type 3 lithium, measured per six carbons, $x_{1o}$, $x_{2o}$, and $x_{3o}$ are initial amounts of lithium after electrochemical discharge and before heating, $E_1$ and $E_2$ are activation energies, and $\gamma_1$ and $\gamma_2$ are frequency factors, f is a constant of proportionality that governs how fast the layer of reaction products on the surface of the carbon grows as type 1 lithium is converted to type 3 lithium, and $H_1$ and $H_2$ are the heat per gram of carbon due to the changes $\Delta x_1 = -1$ and $\Delta x_2 = -1$, respectively.

45. The method of claim 41, wherein:
characterizing the cathode/electrolyte reaction comprises characterizing the cathode/electrolyte reaction using less than about 100 grams of cathode material; and
characterizing the anode/electrolyte reaction comprises characterizing the anode/electrolyte reaction using less than about 100 grams of anode material.

46. The method of claim 41, wherein:
characterizing the cathode/electrolyte reaction comprises characterizing the cathode/electrolyte reaction using between about 1 and about 10 grams of cathode material; and
characterizing the anode/electrolyte reaction comprises characterizing the anode/electrolyte reaction using between about 1 and about 10 grams of anode material.

47. The method of claim 41, wherein:
characterizing the cathode/electrolyte reaction comprises characterizing the cathode/electrolyte reaction using between about 1 milligram and about 1 gram of cathode material; and
characterizing the anode/electrolyte reaction comprises characterizing the anode/electrolyte reaction using between about 1 milligram and about 1 gram of anode material.

48. The method of claim 41, wherein the cathode and anode material each comprises lithium.

49. The method of claim 41, wherein characterizing the first and second power functions comprises obtaining temperature versus time data of each of the cathode/electrolyte and anode/electrolyte reactions.

50. The method of claim 41, wherein characterizing the first and second power functions comprises using a calorimetry technique.

51. The method of claim 50, wherein using the calorimetry technique comprises using an accelerating rate calorimetry technique or a differential scanning calorimetry technique.

52. The method of claim 41, wherein the specified operating condition comprises a condition of constant or varying ambient temperature.

53. The method of claim 41, wherein the specified operating condition comprises a condition of a constant or varying current applied to the cell.

54. The method of claim 41, wherein the specified operating condition comprises a condition of an external short-circuit connected to the cell.

55. The method of claim 41, wherein the specified operating condition comprises a condition of a short-circuit internal to the cell.

56. A computer readable medium embodying program instructions for characterizing electrochemical cell components, comprising:
characterizing a reaction between a cathode and an electrolyte in terms of thermal power per unit mass of cathode material by defining a first power function;
characterizing a reaction between an anode and the electrolyte in terms of thermal power per unit mass of anode material by defining a second power function;
defining one or more physical parameters of the electrochemical cell; and
predicting, using the first and second power functions and the physical parameters of the electrochemical cell, a response of the cell to a specified operating condition.

57. The medium of claim 56, wherein characterizing the respective cathode/electrolyte and anode/electrolyte reactions comprises modeling the respective reactions assuming an autocatalytic reaction mechanism.

58. The method of claim 56, wherein the first power function, $P_c$, associated with the cathode/electrolyte reaction is given by the following equations:

$$\frac{du}{dt} = k(1-u)(\beta + u^{0.5})$$

$$\frac{dT}{dt} = \frac{h}{C'_{tot}} * \frac{du}{dt}$$

$$P_c = H \, du/dt$$

where, u represents a dimensionless fractional degree of conversion, k represents a reaction rate constant defined by $k=\gamma \exp(-E_a/k_b T)$, $\gamma$ represents a frequency factor expressed in terms of minutes$^{-1}$, $E_a$ represents activation energy, $k_b$ represents Boltzmann's constant, T represents a temperature of the cell, $\beta$ represents a dimensionless parameter of autocatalysis, h represents total heat which can be evolved by a sample of cathode material during reaction expressed in terms of Joules, $C'_{tot}$ represents a total heat capacity of the reactant and a sample calorimeter bomb expressed in terms of J/K, and H represent total heat generated by the cathode/electrolyte reaction per gram of cathode material.

59. The medium of claim 56, wherein the second power function, $P_a$, associated with the anode/electrolyte reaction is given by:

$$P_a = H_2 \left| \frac{dx_2}{dt} \right| + H_1 \left| \frac{dx_1}{dt} \right|$$

where, $$\frac{dx_2}{dt} = -\gamma_2 \exp^{-E_2/k_b T} x_2^{0.5}$$

$$\frac{dx_1}{dt} = -\gamma_1 \exp^{-E_1/k_b T} x_1 \exp^{-((x_{3o}+x_{2o})+f(x_{1o}-x_1))/(x_{3o}+x_{2o})} \text{ and}$$

$$\frac{dx_3}{dt} = -\frac{dx_1}{dt} - \frac{dx_2}{dt}$$

further where, $x_1$ represents an amount of type 1 lithium measured as x in $Li_xC_6$, $x_2$ is an amount of type 2 lithium, measured per six carbons, and $x_3$ is an amount of type 3 lithium, measured per six carbons, $X_{1o}$, $x_{2o}$, and $x_{3o}$ are initial amounts of lithium after electrochemical discharge and before heating, $E_1$ and $E_2$ are activation energies, and $\gamma_1$ and $\gamma_2$ are frequency factors, f is a constant of proportionality that governs how fast the layer of reaction products on the surface of the carbon grows as type 1 lithium is converted to type 3 lithium, and $H_1$ and $H_2$ are the heat per gram of carbon due to the changes $\Delta x_1 = -1$ and $\Delta x_2 = -1$, respectively.

60. The medium of claim 56, wherein:
   defining one or more physical parameters of the cell further comprises adjusting the physical parameters of the cell; and
   predicting the response of the cell further comprises predicting the response of the cell using the first and second power functions and the adjusted physical parameters of the cell.

61. The medium of claim 56, wherein defining one or more physical parameters of the cell further comprises receiving user input data representative of physical parameters of the cell.

62. The medium of claim 61, wherein receiving user input data further comprises:

presenting to a user an input field corresponding to each physical parameter of the cell; and
receiving input data from the user in each of the input fields.

63. The medium of claim 56, wherein defining one or more physical parameters of the cell further comprises receiving physical parameters of the cell electronically.

64. The medium of claim 56, wherein defining one or more physical parameters of the cell further comprises defining one or more physical parameters for each of an anode and a cathode of the cell.

65. The medium of claim 64, further wherein:
   defining physical parameters for each of the anode and cathode of the cell further comprises adjusting the physical parameters of one or both of the anode and cathode; and
   predicting the response of the cell further comprises predicting the response of the cell using the first and second power functions and the adjusted physical parameters of one or both of the anode and cathode.

66. The medium of claim 56, wherein the specified operating condition comprises a condition of constant or varying ambient temperature.

67. The medium of claim 56, wherein the specified operating condition comprises a condition of a constant or varying current applied to the cell.

68. The medium of claim 56, wherein the specified operating condition comprises a condition of an external short-circuit connected to the cell.

69. The medium of claim 56, wherein the specified operating condition comprises a condition of a short-circuit internal to the cell.

70. The medium of claim 56, wherein the medium comprises one or more magnetic data storage diskettes, direct access data storage disks, magnetic tape, alterable or non-alterable electronic read-only memory, flash memory, optical storage devices or signal-bearing media comprising digital, analog, and/or communication links and wireless transmission media or propagated signal media.

* * * * *

UNITED STATES PATENT AND TRADEMARK OFFICE
CERTIFICATE OF CORRECTION

PATENT NO. : 6,833,707 B1  
APPLICATION NO. : 09/473569  
DATED : December 21, 2004  
INVENTOR(S) : Jeffrey R. Dahn Page 1 of 3

It is certified that error appears in the above-identified patent and that said Letters Patent is hereby corrected as shown below:

Column 5  
Line 56, below " $\frac{dT}{dt} = \frac{h}{C'_{tot}} * \frac{du}{dt}$ " insert - - $P_c = H\, du/dt$ - -.

Column 6  
Lines 7-8, delete "$P_B$" and insert - - $P_a$ - -, therefor.

Line 7-8, after " $P_a = H_2 |\frac{dx_2}{dt}| + H_1 |\frac{dx_1}{dt}|$ " insert - - [13] - -.

Line 11, after " $\frac{dx_1}{dt} = -\gamma_1 \exp^{-E_1/k_b T} x_1$ " insert - - [14] - -.

Line 15, delete "$dx_2$" and insert - - $dx_1$ - -, therefor.

Line 15, delete "$-E_2/k_b T$" and insert - - - $E_1/k_b T$ - -, therefor.  
Line 15, after "and" insert - - [15] - -.  
Line 38, delete " cathodelelectrolyte" and insert - - cathode/electrolyte - -, therefor.

Column 11  
Line 25-27, Delete "The accelerating rate calorimeter 100 maintains a sample in adiabatic conditions once an exothermic reaction has been detected and measures sample temperature as a function of time." and insert the same on line 24 after "(model ARC-2000)".

Column 11  
Line 53, after "of" delete "a".

Column 12  
Line 53, after "onset" insert - - . - -.

Column 13  
Line 44, delete "fill" and insert - - full - -, therefor.

Column 15  
Line 63, after "K" insert - - . - -.

Column 18  
Line 11, after "[14]" insert - - , - -.  
Line 14, delete "$-E_2/k_b T$" and insert - - - $E_1/k_b T$ - -, therefor.

UNITED STATES PATENT AND TRADEMARK OFFICE
CERTIFICATE OF CORRECTION

PATENT NO. : 6,833,707 B1
APPLICATION NO. : 09/473569
DATED : December 21, 2004
INVENTOR(S) : Jeffrey R. Dahn It is certified that error appears in the above-identified patent and that said Letters Patent is hereby corrected as shown below:

Column 19
Line 21, delete "$[P_{ai}\rho_a+P_{ci}\rho_c+P_{ci}]$" and insert - - $[P_{ai}\rho_a+P_{ci}\rho_c+P_{ei}]$ - -, therefor.
Line 49, delete "$[P_{ai}\rho_a+P_{ci}\rho_c+P_{ci}]$" and insert - - $[P_{ai}\rho_a+P_{ci}\rho_c+P_{ei}]$ - -, therefor.
Line 61, delete "$(T_c - T_{can})$" and insert - - $(T_e - T_c)$ - -, therefor.
Line 66, delete "envirornmental" and insert - - environmental - -, therefor.

Column 21
Line 6, delete "$(T_e - T_{can})$" and insert - - $(T_e - T_c)$ - -, therefor.
Line 13, delete "$T_c$" and insert - - $T_e$ - -, therefor.
Line 14, delete "$X_3$;" and insert - - $x_{3i}$ - -, therefor.

Column 23
Line 36, delete "y" and insert - - $\gamma$ - -, therefor.
Line 61, delete "an d" and insert - - and - -, therefor.

Column 27
Line 18, after "302" delete ";" and insert - - . - -, therefor.
Line 51, delete "xio" and insert - - Xio - -, therefor.
Line 60, delete "$^0$c.)" and insert - - ($^0$c.) - -, therefor.

Column 28
Line 20-25, delete "Figure 19 shows a Cylindrical Calculation dialog box 400 which is presented to the designer in response to activating the Cylindrical Geometry button 392 provided in the Battery Geometry region 390. The designer may enter can length (cm) and radius (cm) values using Length and Radius input fields 402 and 404, respectively." and insert the same on line 19 after "394.".

UNITED STATES PATENT AND TRADEMARK OFFICE
CERTIFICATE OF CORRECTION

PATENT NO. : 6,833,707 B1
APPLICATION NO. : 09/473569
DATED : December 21, 2004
INVENTOR(S) : Jeffrey R. Dahn It is certified that error appears in the above-identified patent and that said Letters Patent is hereby corrected as shown below:

Column 29
Line 16, insert - - Alternatively, the instructions may be contained in other signal-bearing media, such as one or more magnetic data storage diskettes, direct access data storage disks (e.g., a conventional hard drive or a RAID array), magnetic tape, alterable or non-alterable electronic read-only memory (e.g., EEPROM, ROM), flash memory, optical storage devices (e.g., CDROM or WORM), signal-bearing media including transmission media such as digital, analog, and communications links and wireless, and propagated signal media (e.g., via communications link 129). In an illustrative embodiment, the machine-readable instructions may constitute lines of compiled "C" language code or "C++" object-oriented code. - - in line 16 as a new paragraph.

Signed and Sealed this

Twenty-sixth Day of September, 2006

JON W. DUDAS
*Director of the United States Patent and Trademark Office*